United States Patent
Sirovatka et al.

(10) Patent No.: US 7,884,037 B2
(45) Date of Patent: Feb. 8, 2011

(54) WET WIPE HAVING A STRATIFIED WETTING COMPOSITION THEREIN AND PROCESS FOR PREPARING SAME

(75) Inventors: Kathryn Sirovatka, Neenah, WI (US); Keisha Clarke, Appleton, WI (US); Scott Wenzel, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1089 days.

(21) Appl. No.: 11/611,666

(22) Filed: Dec. 15, 2006

(65) Prior Publication Data

US 2008/0145664 A1 Jun. 19, 2008

(51) Int. Cl.
*B32B 27/12* (2006.01)
(52) U.S. Cl. .................................... 442/102; 442/327
(58) Field of Classification Search ................ 442/102, 442/149, 327
See application file for complete search history.

(56) References Cited

U.S. PATENT DOCUMENTS

| | | | |
|---|---|---|---|
| 3,554,862 A | 1/1971 | Hervey et al. |
| 4,144,122 A | 3/1979 | Emanuelsson et al. |
| 4,460,406 A | 7/1984 | Valange |
| 4,476,323 A | 10/1984 | Hellsten et al. |
| 4,559,157 A | 12/1985 | Smith et al. |
| 4,667,890 A | 5/1987 | Gietman, Jr. |
| 4,690,821 A | 9/1987 | Smith et al. |
| 4,775,489 A | 10/1988 | Watkins et al. |
| 4,883,659 A | 11/1989 | Goodman et al. |
| 4,904,524 A | 2/1990 | Yoh |
| 5,043,155 A | 8/1991 | Puchalski |
| 5,312,883 A | 5/1994 | Komatsu et al. |

(Continued)

FOREIGN PATENT DOCUMENTS

EP 0407041 B1 1/1991

(Continued)

OTHER PUBLICATIONS

New Airlaid Binders, Nonwovens Report International, 342: 20-22 and 28-31 (Sep. 1999).

(Continued)

*Primary Examiner*—Lynda Salvatore
(74) *Attorney, Agent, or Firm*—Armstrong Teasdale LLP

(57) ABSTRACT

The present invention generally relates to a wet wipe or sheet that is suitable for contacting the skin and that has a stratified wetting composition therein. More specifically, the present invention related to a wet wipe, which may optionally be an ion-triggerable, water-disintegratable wipe, wherein the organic phase, and more particularly one or more components of the organic phase, of the wetting composition is concentrated near the surface of the wipe, and the aqueous phase of the wetting composition is concentrated in the bulk of the wipe. The present invention is further directed to a number of processes for preparing such a wet wipe. For example, in one embodiment an emulsified wetting composition is applied to a fibrous substrate of the wet wipe, and then treated to destabilize the emulsion. In an alternative embodiment, an emulsified wetting composition may be destabilized prior to it being applied to the fibrous substrate. As a result of the destabilization, the emulsion undergoes phase separation after being applied to the fibrous substrate.

20 Claims, 1 Drawing Sheet

U.S. PATENT DOCUMENTS

| | | | |
|---|---|---|---|
| 5,317,063 | A | 5/1994 | Komatsu et al. |
| 5,384,189 | A | 1/1995 | Kuroda et al. |
| 5,573,637 | A | 11/1996 | Ampulski et al. |
| 5,756,106 | A | 5/1998 | Concannon et al. |
| 5,871,762 | A | 2/1999 | Venkitaraman et al. |
| 5,969,038 | A | 10/1999 | Fecht et al. |
| 5,972,805 | A | 10/1999 | Pomplun et al. |
| 5,986,004 | A | 11/1999 | Pomplun et al. |
| 6,043,317 | A | 3/2000 | Mumick et al. |
| 6,051,749 | A | 4/2000 | Schulz |
| 6,083,854 | A | 7/2000 | Bogdanski et al. |
| 6,194,517 | B1 | 2/2001 | Pomplun et al. |
| 6,231,843 | B1 | 5/2001 | Hoelzel et al. |
| 6,291,372 | B1 | 9/2001 | Mumick et al. |
| 6,299,780 | B1 | 10/2001 | Freshour et al. |
| 6,410,039 | B1 | 6/2002 | Walker |
| 6,423,804 | B1 | 7/2002 | Chang et al. |
| 6,429,261 | B1 | 8/2002 | Lang et al. |
| 6,436,234 | B1 | 8/2002 | Chen et al. |
| 6,444,214 | B1 | 9/2002 | Cole et al. |
| 6,537,663 | B1 | 3/2003 | Lang et al. |
| 6,548,100 | B1 | 4/2003 | Bauer et al. |
| 6,548,592 | B1 | 4/2003 | Lang et al. |
| 6,579,570 | B1 | 6/2003 | Lang et al. |
| 6,586,033 | B1 | 7/2003 | Gimelli et al. |
| 6,586,529 | B2 | 7/2003 | Mumick et al. |
| 6,596,336 | B1 | 7/2003 | Gimelli et al. |
| 6,599,848 | B1 | 7/2003 | Chen et al. |
| 6,602,955 | B2 | 8/2003 | Soerens et al. |
| 6,626,961 | B1 | 9/2003 | Everhart et al. |
| 6,630,558 | B2 | 10/2003 | Chang et al. |
| 6,653,406 | B1 | 11/2003 | Soerens et al. |
| 6,683,143 | B1 | 1/2004 | Mumick et al. |
| 6,713,414 | B1 | 3/2004 | Pomplun et al. |
| 6,747,124 | B2 | 6/2004 | Eichenauer et al. |
| 6,815,502 | B1 | 11/2004 | Lang et al. |
| 6,828,014 | B2 | 12/2004 | Branham et al. |
| 6,835,678 | B2 | 12/2004 | Jackson et al. |
| 6,855,790 | B2 | 2/2005 | Chang et al. |
| 6,897,168 | B2 | 5/2005 | Branham et al. |
| 6,908,966 | B2 | 6/2005 | Chang et al. |
| 6,960,371 | B2 | 11/2005 | Bunyard et al. |
| 6,994,865 | B2 | 2/2006 | Branham et al. |
| 7,141,519 | B2 | 11/2006 | Bunyard et al. |
| 2002/0081930 | A1 | 6/2002 | Jackson et al. |
| 2002/0155281 | A1 | 10/2002 | Lang et al. |
| 2003/0027470 | A1 | 2/2003 | Chang et al. |
| 2003/0045191 | A1 | 3/2003 | Goldstein et al. |
| 2003/0147825 | A1 | 8/2003 | Chiarelli et al. |
| 2004/0063888 | A1 | 4/2004 | Bunyard et al. |
| 2005/0009431 | A1 | 1/2005 | Chamba et al. |
| 2005/0238610 | A1 | 10/2005 | Nielsen et al. |
| 2006/0204468 | A1 | 9/2006 | Allef et al. |
| 2006/0252876 | A1 | 11/2006 | Farwaha et al. |
| 2006/0252877 | A1 | 11/2006 | Farwaha et al. |

FOREIGN PATENT DOCUMENTS

| | | |
|---|---|---|
| EP | 0408199 A1 | 1/1991 |
| EP | 608460 A1 | 8/1994 |
| EP | 0610039 A1 | 8/1994 |
| EP | 0578620 B1 | 12/1994 |
| EP | 0693349 A1 | 1/1996 |
| EP | 1059378 A1 | 12/2000 |
| JP | 2251239 A | 10/1990 |
| JP | 4200631 A | 7/1992 |
| JP | 11035447 A | 2/1999 |
| JP | 11106310 A | 4/1999 |
| JP | 2000128724 A | 5/2000 |
| JP | 2000233455 | 8/2000 |
| JP | 2002246794 A | 8/2002 |
| WO | 9207551 A1 | 5/1992 |
| WO | 9826808 A2 | 6/1998 |
| WO | 2005004835 A1 | 1/2005 |

OTHER PUBLICATIONS

S. Lee et al., "Antimicrobial and Blood Repellent Finishes for Cotton and Nonwoven Fabrics Based on Chitosan and Fluoropolymers," Textile Research J., 69(2): 104-112 (Feb. 1999).

Office action from U.S. Appl. No. 11/611,616, dated Apr. 21, 2008.

Final Office Action, U.S. Appl. No. 11/611,616, (Mar. 20, 2009).

International Search Report and Written Opinion regarding PCT/IB2007/054639, dated May 6, 2008.

International Search Report and Written Opinion from PCT/IB2007/054641, dated May 8, 2006.

WET WIPE HAVING A STRATIFIED WETTING COMPOSITION THEREIN AND PROCESS FOR PREPARING SAME

BACKGROUND OF INVENTION

The present invention generally relates to a wet wipe or sheet that is suitable for contacting the skin and that has a stratified wetting composition therein. More specifically, the present invention related to a wet wipe, which may optionally be an ion-triggerable, water-disintegratable wipe, wherein the organic phase, and more particularly one or more components of the organic phase, of the wetting composition is concentrated near the surface of the wipe, and the aqueous phase of the wetting composition is concentrated in the bulk of the wipe. The present invention is further directed to a number of processes for preparing such a wet wipe. For example, in one embodiment an emulsified wetting composition is applied to a fibrous substrate of the wet wipe, and then treated to destabilize the emulsion. In an alternative embodiment, an emulsified wetting composition may be destabilized prior to it being applied to the fibrous substrate. As a result of the destabilization, the emulsion undergoes phase separation after being applied to the fibrous substrate.

Water-disintegratable (i.e., flushable) wet wipes are now generally known in the art. For example, binder compositions have been developed for use in such wipes which are more dispersible and are more environmentally responsible than past binder compositions. In particular, various ion-triggerable binder systems have been identified as advantageous because they enable the base sheet of the water-disintegratable wipe to remain strong in the dry state, and further help to maintain a desired level of strength in the wet state, yet allow the wipe to disintegrate or disperse upon disposal by means of "ion triggerability." In a common embodiment, such a binder is applied onto an airlaid web of fibers (e.g., cellulose fibers) that make up the wipe, and then the treated fibers are dried. A wetting solution or composition, which contains a controlled concentration of a salt (or more generally an "insolublizing agent") in water, is typically then applied to the base sheet, which acts to insolublize the binder due to the salt present therein. These binders have a "triggerable" property, in that they are (1) rendered insoluble upon treatment with the wetting composition that contains a salt (or insolublizing agent) of a particular type and/or concentration, but (2) solubilized, and thus disintegrate, when the salt is diluted by contact with a diluting-amount of water, including for example hard water (e.g., water having 200 parts per million (ppm), or more, of calcium or magnesium ions). After being contacted with, or diluted by, the water, the web of fibers that make up the wipe breaks apart or separates into smaller pieces and disperses.

One class of ion-sensitive binders which are suitable for use in water-disintegratable wipes is acrylic acid-based terpolymers, which comprise partially neutralized acrylic acid, butyl acrylate and 2-ethylhexyl acrylate. Such polymers are disclosed in, for example, U.S. Pat. Nos. 5,312,883; 5,317,063; and 5,384,189; as well as European Patent No. 608460A1. However, because of the presence of a small amount of sodium acrylate in the partially neutralized terpolymer, such binders typically fail to disperse in hard water (e.g., water containing more than about 15 ppm calcium ions ($Ca^{2+}$) and/or magnesium ions ($Mg^{2+}$)). As a result, the application of the terpolymer as a dispersible binder in such wipes is limited in some parts of the world, including for example the U.S., which has hard water in many parts of the country. Related to the foregoing, U.S. Pat. No. 6,423,804 (assigned to Kimberly Clark) discloses sulfonate anion modified acrylic acid terpolymers which have improved dispersibility in relatively hard water (i.e., water having up to 200 ppm $Ca^{2+}$ and/or $Mg^{2+}$, compared to the unmodified polymers). Additionally, U.S. Pat. No. 6,994,865 (assigned to Kimberly Clark), describes an ion-triggerable binder composition comprising the polymerization product of a vinyl-functional cationic monomer and one or more hydrophobic vinyl monomers with alkyl side chains of 1 to 4 carbon atoms.

Other examples of ion triggerable polymeric binders exist, including for example those disclosed in U.S. Published application Nos. 2006/0252876 and 2006/0252877.

Known wetting compositions or solution for these ion-triggerable, water-disintegratable wipes are generally solution-based (see, e.g., the composition described in U.S. Pat. No. 6,444,214). Solution-based systems have, to-date, been limited in terms of the types of ingredients or components that can be incorporated therein. Additionally, the hand-feel that can be obtained with solution-based wipes is limited, again due to the limitations on the types of ingredients or components that can be used in the wetting compositions. These limitations result, at least in part, because the aqueous salt-solutions that are the base, or primary component, of the wetting composition are not compatible with (e.g., they phase separate from) the desirable organic (or hydrophobic), skin-beneficial materials.

For these reasons, it is desirable to use a wetting composition that is in the form of an oil-in-water emulsion. Emulsions are desirable as wetting compositions for use in wet wipes, particularly ion-triggerable, water-disintegratable wet wipes, because they enable the incorporation of ingredients with skin benefits, such as emollients, therein, and because they can produce a desired effect (e.g., a characteristic smooth hand feel). However, the ingredient or component used to produce the desired result, and/or the emulsifier used to produce a suitable emulsion, can be expensive, particularly when they are to be used with a base sheet for an ion-triggerable, water-disintegratable wet wipe. Furthermore, the use of such emulsions can result in the skin beneficial ingredients being distributed throughout the wipe rather than being concentrated at the wipe surface, where they can be the most effective. As a result, an excessive amount of these ingredients may be needed to achieve the desired result, which acts to increase the overall cost of the wipe.

Accordingly, a need exists for a wetting composition that is sufficiently stable such that skin beneficial ingredients, which are often organic (or oil-based), may be added to the base sheet of the wipe in liquid form, but that subsequently concentrate themselves at the wipe surface, or near the wipe surface, in order to increase their effectiveness.

SUMMARY OF THE INVENTION

The present invention is generally directed to a wet wipe that comprises a stratified wetting composition, and/or to a process for the preparation thereof. The present invention therefore provides a more economical, or less expensive, wet wipe that maximizes the use of skin beneficial ingredients present in the wetting composition, by concentrating them at or near the surface(s) of the wipe.

The process of the present invention is particularly well-suited for the preparation of an ion-triggerable, water-disintegratable wipe that comprises the stratified wetting composition. As such, the wipes may additionally include a triggerable binder formulation that provides the strength of the wipe in the dry state, and helps to maintain a desired level of strength of the fibrous substrate of the wipe in the wet state, yet allows the wipe to disintegrate or disperse upon disposal by means of "ion-triggerability." Other optional components suitable for use in a stratified wetting composition include, for example, anti-microbial agents, pharmaceutical or treatment agents, and additional additives (as detailed elsewhere herein).

It is to be noted that, for an ion-triggerable, water-disintegratable wet wipe, a controlled concentration of a suitable salt (or more generally an insolublizing agent) in the wetting composition (e.g., in the emulsified wetting composition, or the wetting composition prior to stratification) may act to render the binder formulation insoluble, thus allowing the binding agent to function as an adhesive for the fibers. The binder formulation therefore may have a "triggerable property" in that, when the wipe is discarded into a wastewater stream (including for example hard water having a given concentration, such as 200 ppm or more of, for example, calcium and magnesium ions), the concentration of the insolublizing agent is diluted, which in turn results in the triggerable binder formulation becoming soluble and the strength of the fibrous substrate dropping below a critical level. This allows the fibrous substrate of the wipe to break apart into small pieces and, ultimately, disperse.

The wetting composition (e.g., the emulsified wetting composition, or the stratified wetting composition formed therefrom), as well as the triggerable binder formulation, are well-suited for use with airlaid and wet-laid fibrous substrates, such as nonwoven fabrics, for various applications, including for example cleaning, hard surface cleaning, disinfecting, sanitizing, and personal care products. The wetting composition and triggerable binder formulation are particularly well-suited for use with flushable cleaning and personal care products, particularly wet wipes for personal use, such as cleaning or treating skin or mucosa, make-up removal, nail polish removal, medical care, and also wipes for use in hard surface cleaning, automotive care, including wipes comprising cleaning agents, disinfectants, and the like. The flushable cleaning or personal care products maintain integrity or wet strength during storage and use, and break apart or disperse after disposal in the toilet when the salt concentration falls below a critical level.

As further detailed elsewhere herein, fibrous substrates suitable for treatment with an emulsified wetting composition, as well as the triggerable binder formulation, include, but are not limited to, tissue, such as creped or uncreped tissue, coform products, hydroentangled webs, airlaid mats, fluff pulp, nonwoven webs, and composites thereof. Methods for producing uncreped tissues and molded three-dimensional tissue webs of use in the present invention may be found in, for example, U.S. Pat. No. 6,436,234.

The emulsified wetting composition may optionally be in concentrated form, the concentrated emulsion being for example diluted with water, or a salt-containing aqueous solution, or an acid-containing aqueous solution, or a base-containing aqueous solution, prior to use. In such instances, the resulting diluted, emulsified wetting composition may be applied to fibrous substrate and then treated in some way to destabilize the emulsion to cause phase separation to occur (e.g., phase separation occurring within less than about 1 week and more than about 10 minutes), or the diluted, emulsified wetting composition itself may already be destabilized, or treated in some way to destabilize it, such that phase separation occurs after application to the base sheet (e.g., the act of diluting the concentrated emulsion itself may result in destabilization of the emulsion, such that phase separation occurring within less than about 1 week and more than about 10 minutes, after application to the fibrous substrate).

Briefly, therefore, the present invention is directed to a wet wipe comprising a stratified wetting composition therein. More particularly, the present invention is directed to such a wet wipe comprising: (i) a fibrous substrate having a top surface and a bottom surface, and surface regions extending inwardly from the top and bottom surfaces, and a bulk region between the top near surface region and the bottom near surface region; and, (ii) a wetting composition in contact with the fibrous substrate, the wetting composition comprising an oil phase and an aqueous phase, wherein a concentration of one or more oil phase components is greater in the front and back surface regions of the substrate than a concentration of the same component, or components, in the bulk region (i.e., non-surface region) of the substrate, and further wherein a concentration of one or more aqueous phase components is greater in the bulk region of the substrate than a concentration of the same component, or components, in the front and back surface regions of the substrate (based on the total weight of the particular component, or components, or phase, in the wetting composition). Optionally, the wipe may further comprise a binder formulation that is insoluble in the wetting composition and dispersible in water, said wipe being an ion-triggerable, water-dispersible wipe.

The present invention is further directed to various processes for preparing a wet wipe product comprising a stratified wetting composition. In general, the process may involve the application of a dilute oil-in-water emulsified wetting composition to the fibrous substrate of the wipe and then acting upon the wipe in some way to destabilize the wetting composition therein (such that phase separation occurs within less than about 1 week and more than about 10 minutes). Destabilization may be achieved, for example, by heating or chilling (e.g., freezing) the wet wipe. In one particular embodiment, the process may additionally involve the initial formation of the dilute oil-in-water emulsified wetting composition by diluting a concentrated form of the emulsified wetting composition.

Alternatively, the dilute oil-in-water emulsified wetting composition may be destabilized prior to the application thereof to the fibrous substrate. Destabilization may be achieved by heating or chilling the composition, by adjusting the pH thereof (e.g., the addition of an acid or a base thereto), or by adding salt thereto. In one particular embodiment, the process may additionally involve the initial formation of the dilute oil-in-water emulsified wetting composition by diluting a concentrated form of the emulsified wetting composition. In fact, in one such process the dilution step and the destabilization step may be the same (e.g., a concentrated form of the emulsified wetting composition may be diluted with a salt solution, an acid solution, or a basic solution, in order to form a dilute, destabilized oil-in-water emulsified wetting composition).

Alternatively, the wipe may be prepared by contacting the fibrous substrate with a concentrated form of the oil-in-water emulsified wetting composition. An aqueous solution is also applied to the fibrous substrate, either before or after application of the concentrated form of the oil-in-water emulsified wetting composition, in order to form a dilute, oil-in-water emulsified wetting composition in situ therein. The dilute, oil-in-water emulsified wetting composition may then be destabilized in some way (e.g., by heating or chilling the wipe). Alternatively, a dilute, destabilized oil-in-water emulsified wetting composition may be formed in situ within the wipe, wherein the act of dilution (by contacting the concentrated form of the oil-in-water emulsified wetting composition with the aqueous solution) also results in destabilization.

In yet another alternative embodiment, the wipe may be prepared by contacting the fibrous substrate with an organic (or oil) based liquid and an aqueous (or water) based liquid, which are not in the form of an emulsion and do not form a stable emulsion. After a period of time, these liquids migrate to the surface (or surface regions) and the bulk region, respectively, to form a wet wipe having a stratified wetting composition therein.

In yet another alternative embodiment, the wipe may be prepared by destabilizing the oil-in-water emulsion, either before or after it has been applied to the fibrous substrate, using some other means known to one of ordinary skill in the art for breaking an emulsion (see, e.g., means disclosed in McGraw Hill Concise Encyclopedia of Science and Technology, which references, for example, (i) applying a high potential alternating current or electric field to the wipe or emulsion, (ii) treating the wipe or emulsion with ultrasonic energy or waves of low intensity, and/or (iii) adding multivalent ions to the wipe or emulsion having a charge opposite to that of the emulsion droplets).

It is to be noted that, regardless of the method utilized to form the wet wipe of the present invention, preferably phase separation occurs within the fibrous substrate within less than about 1 week and more than about 10 minutes.

It is to be further noted that, in one or more of the above embodiments, the dilute, oil-in-water emulsified wetting composition may have a salt concentration of at least about 0.5 weight percent, based on the total weight of the emulsified wetting composition, prior to said destabilizing treatment, or after (even as a result of) said destabilization treatment. Additionally, in this or another embodiment, said process may comprise contacting the fibrous substrate with a triggerable binder formulation prior to said wetting composition, wherein said triggerable binder formulation is insoluble in the emulsified wetting composition and dispersible in water.

Other features will be in part apparent and in part pointed out hereinafter.

Figure 1:
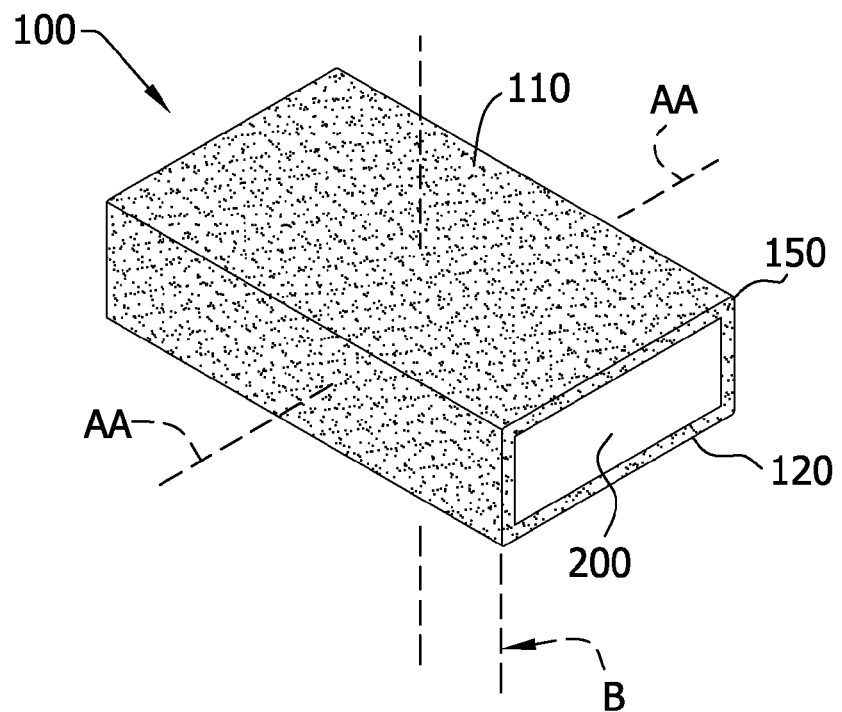
FIG. 1 illustrates a perspective view of a wet wipe, as further detailed herein below.

It is to be noted that the figures presented herein are provide for illustration, and therefore are not necessarily to scale (either within a given figure, or from one figure to another). Additionally, it is to be noted that corresponding reference characters indicate corresponding parts throughout the figures.

DETAILED DESCRIPTION OF THE INVENTION

In accordance with the present invention, a more cost effective wet wipe, which may optionally be in the form of an ion-triggerable, water-disintegratable wet wipe, has been discovered, the wipe having a stratified wetting composition which imparts an improved handfeel, delivers active skin-beneficial ingredients, improves moisturization, and/or enhances transfer of formulation or active ingredients to the skin, by means of concentrating the skin beneficial ingredients therein on, or in a region near, the surface of the wipe. As further detailed herein below, the wipe may be prepared by a number of different processes. For example, in one embodiment, a wetting composition in the form of an oil-in-water emulsion, such as a low viscosity oil-in-water emulsion, that is designed to remain stable for an extended period of time, including for example an emulsion that remains stable in the presence of a high salt concentration therein, is applied to a fibrous substrate, and then subsequently acted upon in some way to destabilized the emulsion. As a result, phase separation of the emulsion occurs, the organic (or oil) phase migrating to the surface, or to a near surface region, in the fibrous substrate and the aqueous (or water) phase migrating to or remaining in a bulk region of the fibrous substrate (e.g., an interior region of the substrate that does not include the surfaces, or the near surface regions, thereof). In an alternative embodiment, this wetting composition may be acted upon in some way to destabilize the emulsion prior to the fibrous substrate being contacted or wetted therewith, such that phase separation of the wetting composition occurs in the fibrous substrate after the destabilized emulsion has been applied thereto. In yet another alternative embodiment, no oil-in-water emulsion is employed; rather, an organic liquid and an aqueous liquid are mixed thoroughly before being applied jointly to the fibrous substrate and allowed to separate therein in a similar manner.

Regardless of the way in which the wipe is formed, and/or the way in which the destabilized emulsion is formed (e.g., destabilization before or after application of the emulsion to the fibrous substrate), it is preferred in at least some embodiments that the wetting composition (stable or destabilized) be applied to the fibrous substrate in emulsified form; that is, it is preferable that the wetting composition be applied before phase separation begins. This because it is generally believed that application of a homogenous emulsion of the wetting composition to the fibrous substrate is easier and/or more efficient.

It is also to be noted, and without being held to any particular theory, that it is generally believed that phase separation occurs at least in part because of the composition of the fibrous substrate or base sheet of the wet wipe, which is typically hydrophilic. As a result, the organic (or hydrophobic) phase of the emulsion, once the emulsion is broken or begins to phase separate, is repelled by the hydrophilic nature of the base sheet, and therefore migrates to the surface (or near the surface) of the wipe. By taking advantage of the natural repulsion between the organic phase of the wetting composition and the fibrous substrate, the skin-beneficial components, present in the organic phase of the wetting composition, can be concentrated on the surface (or near the surface) of the wipe. Accordingly, the benefit of these components can be maximized, and thus a higher percentage of these components can be transferred from the wipe to the skin. Optionally, the present invention enables less of these components to be used in preparing the wetting composition. A more economical wetting composition can therefore be prepared.

It has been further discovered that, in one or both of the above-noted embodiments, such wipes may be advantageously prepared by optionally using a concentrated form of the emulsion, thus reducing, for example, costs associated with the storage and/or transport of a more dilute emulsion. More specifically, a concentrated emulsion may be prepared and, in the first embodiment noted above, diluted prior to being applied to the fibrous substrate and then destabilized in some way (e.g., the concentrated emulsion being diluted for example with an aqueous salt solution just prior to contacting the fibrous substrate or base sheet of the wipe). In the second embodiment noted above, the acts of dilution and destabilization prior to applying the emulsion to the fibrous substrate may occur in separate steps (e.g., dilution followed by destabilization, or vice versa), or these may occur in a single step (e.g., diluting the concentrated emulsion with a solution that also acts to destabilize the resulting, diluted emulsion, such as by the addition of an aqueous salt solution of some kind).

As previously noted, the wetting composition may contain, in the case of a water-dispersible wipe for example, a salt, or more generally an insolublizing agent, that acts to maintain the strength of a water-dispersible, or "ion-triggerable," binder in the wipe until the salt, or insolublizing agent, is diluted with a sufficient quantity of water, whereupon the strength of the binder begins to decay. The binder is therefore ion-sensitive, such as an ion-sensitive polymeric composition (e.g., cationic polymer composition), as further detailed herein below. Similarly, the insolublizing agent in the wetting composition can be essentially any agent known in the art to be suitable for the particular binder employed in the wipe, or vice versa, including the various salts known to be suitable for use with the various triggerable binders known in the art (e.g., salts having monovalent or multivalent ions, or a blend thereof), or more generally any compound that provides in-use and storage strength to the water-dispersible binder composition, and that can be diluted in water to permit dispersion of the substrate as the binder polymer triggers to a weaker state.

Accordingly, it is to be noted that, as used herein, "ion-triggerable" generally refers to a wipe containing a binder that is (1) rendered insoluble upon treatment with a wetting composition that contains a salt (or insolublizing agent) of a particular type and/or concentration, and (2) solublized, and thus disintegrate, when the salt is diluted by contact with a diluting-amount of water, including for example hard water (e.g., water having 200 parts per million (ppm), or more, of calcium or magnesium ions). After being contacted with, or diluted by, the water, the web of fibers that make up the wipe breaks apart or separates into smaller pieces and disperses.

As further detailed herein below, the wetting composition may optionally comprise a variety of other additives, provided they are compatible with the insolublizing agent and/or the ion-triggerable, water-dispersible binder. For example, suitable additives in the wetting composition may include, but are not limited to, the following: skin-care additives; odor control agents; detackifying agents to reduce the tackiness of the binder; particulates; antimicrobial agents; preservatives; wetting agents and cleaning agents, such as detergents, surfactants, some silicones; emollients; surface feel modifiers for improved tactile sensation (e.g., lubricity) on the skin; fragrance; fragrance solublizers; opacifiers; fluorescent whitening agents; UV absorbers; pharmaceuticals; chelators; humectants; stabilizers; oxidizers; pH control agents, such as malic acid or potassium hydroxide; or some combination thereof.

When an ion-triggerable, water-disintegratable wet wipe is to be prepared, the ion-sensitive or triggerable cationic polymer binder formulation further detailed elsewhere herein, is desirably: (1) functional (e.g., it maintains wet strength under controlled conditions and dissolves or disperses in a reasonable period of time in soft or hard water, such as the water found in toilets and sinks around the world; (2) safe (e.g., not toxic); and/or (3) relatively economical. In addition to the foregoing properties, it is also desirable that the ion-sensitive or triggerable binder composition, when used as a binder for a non-woven substrate of the wet wipe: (4) is processable on a commercial scale (e.g., it may be applied relatively quickly on a large scale basis, such as by spraying, coating, printing and the like, the binder composition thus having a relatively low viscosity at, for example, a high shear); (5) provides acceptable levels of sheet or substrate wettability; (6) provides acceptable levels of sheet or fibrous substrate stiffness; and/or (7) reduces tackiness of the fibrous substrate, or the product that the fibrous substrate is incorporated therein. The wetting composition with which the wipes are treated may help to impart some of the foregoing properties or advantages, and, in addition, may act to: (8) improve skin care, such as reduced skin irritation, delivery of a skin health ingredient, or other benefits, (9) improve tactile properties of the wipe, and/or (10) promote good cleaning, disinfecting, sanitizing properties, by for example providing a balance in use between friction and lubricity on the skin (e.g., skin glide).

A. Wet Wipe having a Stratified Wetting Composition Therein

As previously noted, the present invention is, in part, directed to a wet wipe having, in general, a wetting composition that is stratified therein; that is, the wipe has a wetting composition wherein the organic portion, or phase, thereof is concentrated at or near the surface of the wipe, while the aqueous portion, or phase, is concentrated in the interior, or bulk, of the wipe. More specifically, and referring now to FIGS. 1 and 2, the present invention is directed to a wet wipe 100 that has a top or front surface 110, and a bottom or back surface 120 that is generally parallel to the top or front surface. The front and back surfaces are generally perpendicular to a central axis B extending therethrough.

In one embodiment, after being contacted with a wetting composition (as further detailed elsewhere herein), the composition phase separates with at least a portion of the oil phase separating from the bulk of the emulsion. As a result, the separated organic portion or phase of the wetting composition migrates toward the various surfaces of the wipe, and concentrates in a region 150 near thereto (see, e.g., front surface region 160 and back surface region 170, which extend inwardly toward the center of the wipe from their respective surfaces), while the aqueous portion or phase of the wetting composition migrates toward, or remains in, the non-surface region (i.e., the bulk region, which is bound by the noted surface regions) 200 of the wipe. As a result, after a given period of time (as further detailed elsewhere herein), the fluid in the near surface region 150 of the wipe is richer in, or has a higher concentration of, organic phase components than the bulk fluid. For example, the relative concentration of one or more oil phase components near the surface (e.g., in the front and/or back surface regions 160 and 170, respectively) of the wipe may be about 15% greater, about 25% greater, about 35% greater, or even more, than the average concentration of said oil phase component(s) in the wipe.

Surface chemical analysis techniques can be used to determine the surface concentration of one or more organic phase components. Two valuable techniques are X-Ray Photoelectron Spectroscopy and Attenuated Total Reflectance Infrared Spectroscopy. Photoacoustic Infrared Spectroscopy, Secondary Ion Mass Spectrometry, and other known surface analysis techniques may also be of use. Some surface analysis techniques are conducted under vacuum. In these cases, prior to testing, the wipe sample should be dried rapidly under vacuum prior to analysis. While specific manner of analysis will depend on the analytical technique chosen, by way of example, the ratio of organic phase component or components to a non-volatile component of the aqueous phase (such as for example, a salt or a preservative) can be determined and compared to a theoretical value that would be expected from a homogeneous wipe formulation, or alternately compared to a value derived from a non-stratified wipe. Accordingly, the wipes of the invention will have an organic to aqueous phase component ratio that is 15% greater, 25% greater, 35% greater, or even more than the theoretical value or the value derived from the stratified wipe.

Figure 2:
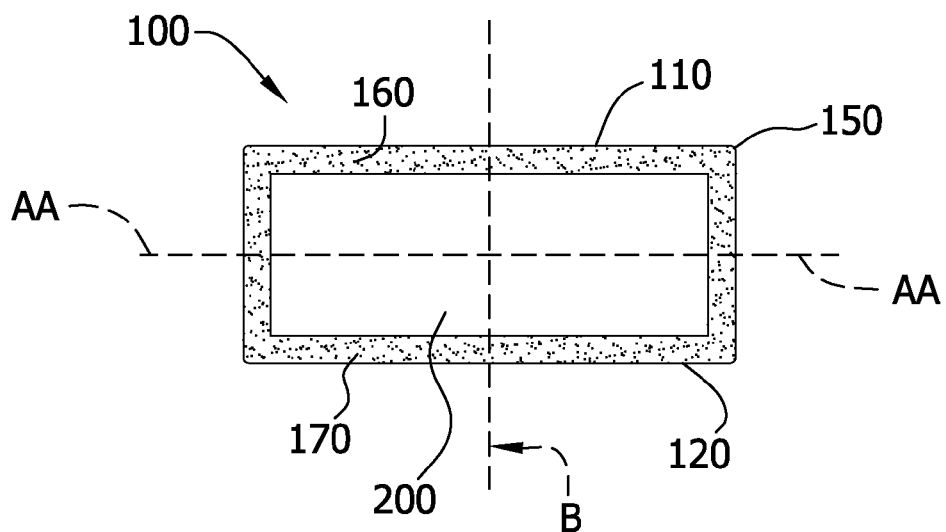
FIG. 2 illustrates a perspective, cross-sectional view of the wipe in FIG. 1 (the cross-section taken along line AA, noted therein), as further detailed herein below.

In this regard it is to be noted that the wipe in FIGS. 1 and 2, as well as the description thereof provided herein, is for purposes of illustration and may be other than herein described without departing from the scope of the present invention.

B. Emulsified Wetting Composition

1. Stability and Viscosity

The present invention utilizes a wetting composition, which may be in the form of an oil-in-water emulsion, and which may be in a stable, or alternatively a semi-stable or destabilized, form when applied to the fibrous substrate of the wipe. In one embodiment, for example, the destabilized oil-in-water emulsion may be formed by mixing a stable emulsion (for example, a concentrated emulsion) with a salt solution, such that the salt concentration in the resulting diluted oil-in-water emulsion is sufficient to cause destabilization therein. Such a wipe may be an ion-triggerable, water-disintegratable wipe. Alternatively, the wipe, including an ion-triggerable, water-disintegratable wipe, may comprise, or may be prepared using, a wetting composition in the form of an oil-in-water emulsion which is stable to a high concentration of salt, or more generally monovalent and/or divalent ions, present therein.

In view of the foregoing, therefore, it is to be noted that, in various embodiments, a salt stable oil-in-water emulsion may be used, while in various alternative embodiments an oil-in-water emulsion that is not stable to a high concentration of salt may be used, in a particular wipe, including an ion-triggerable, water-disintegratable wipe.

It is to be further noted that the oil-in-water emulsified wetting composition is considered to be "stable," or in the case of an ion-triggerable, water-disintegratable wipe "salt stable" (i.e., stable to the high salt concentration present therein), when there is essentially no visible signs of phase separation between the organic or oil phase and the aqueous or water phase of the emulsified wetting composition, for instance if there is essentially no visible sign of the oil phase separating from the emulsion and, for example, floating to the top of the water phase after the emulsified wetting composition has been stored at room temperature (e.g., a temperature between about 20° C. and about 25° C.) for at least about 2 week, about 1 month, about 3 months, about 6 months, about 1 year, about 2 years, or more.

It is to be further noted that an oil-in-water emulsified wetting composition is considered to be "destabilized" or "semi-stable" (including the case of an ion-triggerable, water-disintegratable wipe) when, after having being acted upon or treated in some way (as further detailed elsewhere herein) to destabilize or break the emulsion, the composition exhibits visible signs of phase separation between the organic or oil phase and the aqueous or water phase of the emulsified wetting composition, after having been stored at room temperature (e.g., a temperature between about 20° C. and about 25° C.) for less than about 1 week, about 5 days, about 3 days, about 1 day, about 18 hours, or about 12 hours, and optionally greater than about 10 minutes, about 30 minutes, about 1 hour, about 2 hours, about 4 hours or even about 8 hours. For example, the destabilized or semi-stable emulsion may, in some embodiments, after the emulsion has been acted upon or treated in some way, exhibit phase separation after a period of time between less than about 1 week and greater than about 10 minutes, or about 5 days and about 1 hour, or about 3 days and about 4 hours, or about 1 day and about 8 hours.

It is to be still further noted that, although the viscosity of the emulsified wetting composition may be affected by a number of factors, including for example the emulsifier type and/or concentration, the type and/or concentration of the insolublizing agent such as, for instance, salt (in the case of ion-triggerable wipes), the concentration and/or type of optional components present in the oil phase and/or water phase, the ratio (weight or volume) of oil phase to water phase, etc., as used herein, the emulsified wetting composition typically is flowable, which is generally understood to refer to a viscosity of less than about 50,000 centipoises (cps) at low shear (e.g., less than about 5 rpms, 3 rpms, 1 rpms, 0.5 rpms or less), less than about 35,000 cps, or less than about 20,000 sps. Preferably, however, the viscosity is low, which is generally understood to refer to a viscosity of less than about 15,000, less than about 12,000 cps, less than about 10,000 cps, less than about 8,000 cps, less than about 6,000 cps, less than about 4,000 cps, less than about 2,000 cps, less than about 1,000 cps, or less than about 500 cps, at low shear. For example, the emulsion may, in some embodiments, have a low shear viscosity of between about 500 and about 15,000 cps, or about 1,000 and about 12,000 cps, or about 2,000 and about 10,000 cps.

It is to be still further noted that the emulsified wetting composition, in at least one particular embodiment, is shear thinning. This property may be advantageous for a number of reasons, including ease of use in the substrate wetting process step (i.e., the step in the manufacturing process when the base sheet or substrate is contacted with, or wetted by, the emulsified wetting composition, in either stable or destabilized form), and/or ease of use when the finished wipe is actually used to contact the skin. For example, during the manufacturing process, one common method of applying the wetting composition to the base sheet is to drag the base sheet across a bar (e.g., "drool" bar) which is a perforated, fluid-filled tube. The shear generated in this step is expected to reduce the viscosity of the emulsified wetting composition and make it easier for it to penetrate the base sheet structure (i.e., the fibers thereof).

2. Salts, Emulsifiers and Concentrations Thereof

As previously noted above, the present invention is, in part, directed to a wipe that comprises a wetting composition, which may be in the form of an oil-in-water emulsion, and more particularly in the form of a stable or a semi-stable (or destabilized) emulsion, when applied to the fibrous substrate of the wipe. Accordingly, in the case of an ion-triggerable, water-disintegratable wipe, the wipe may comprise, or may be prepared using, a wetting composition that is destabilized in some way (e.g., due to the salt concentration therein, or the pH thereof), or alternatively may comprise, or may be prepared using, a wetting composition that is stable, for example to a high concentration of salt, or more generally monovalent and/or divalent ions, present therein.

As used herein, therefore, the phrase "high salt concentration" (as well as variations thereof) is to be understood to generally refer to an organic or inorganic salt concentration (or more generally an insolublizing agent concentration, or alternatively a monovalent and/or divalent ion concentration), in the wetting composition, which is applied to the base sheet of the wipe, that is sufficient to render the binder composition, also present in the base sheet of the wipe, sufficiently insoluble to the wetting composition (i.e., the salt concentration is at least in part a function of the type of binder composition used in the wipe, and vice versa). Typically, however, the concentration of the organic and/or inorganic salt, containing monovalent and/or divalent ions, is greater than about 0.3 weight percent, based on the total weight of the emulsified wetting composition, and may be greater than about 0.5 weight percent, greater than about 1 weight percent, greater than about 2 weight percent, greater than about 3 weight percent, greater than about 4 weight percent, or even greater than about 5 weight percent, based on the total weight of the emulsified wetting composition, while also typically being less than about 10 weight percent, less than about 8 weight percent, or even less than about 6 weight percent, again based on the total weight of the wetting composition. For example, the salt concentration in the emulsified wetting composition may, in some embodiments, fall within the range of about 0.5 to about 5 weight percent, or about 1 and about 4 weight percent, based on the total weight of the emulsified wetting composition.

Generally speaking, much like the concentration, the type of insolublizing agent used in the emulsified wetting composition may be essentially any agent that is sufficient for purposes of rendering the binder composition insoluble to the wetting composition. In one particular embodiment, however, the insolublizing agent is an organic or inorganic salt capable of forming or generating monovalent ions (e.g., $Na^+$, $K^+$, $Li^+$, $NH_4^+$, and low molecular weight quaternary ammonium compounds, such as those having fewer than about 5 carbon atoms on any side group attached to the nitrogen atom, as well as combinations thereof) and/or divalent ions (e.g., $Zn_2^+$, $Ca_2^+$ and $Mg_2^+$). Such ions may be derived from a number of organic and inorganic salts including, for example: sodium chloride (NaCl), sodium bromide (NaBr), potassium chloride (KCl), ammonium chloride ($NH_4Cl$), sodium sulfate ($NaSO_4$), zinc chloride ($ZnCl_2$), calcium chloride ($CaCl_2$), magnesium chloride ($MgCl_2$), magnesium sulfate ($MgSO_4$), sodium nitrate ($NaNO_3$), sodium methyl sulfate ($NaSO_4CH_3$), or some combination thereof. In at least some embodiments, alkali metal halides are typically the preferred salt due to low cost, high purity, low toxicity and availability. Among these salts, sodium chloride is a particularly preferred salt for use herein.

Suitable emulsifiers may be selected from those generally known in the art, including for example nonionic emulsifiers, anionic emulsifiers, cationic emulsifiers, amphoteric emulsifiers and zwitterionic emulsifiers, as well as in some instances polymeric emulsifiers. Selection of the emulsifier may depend upon, for example, the way in which the emulsified wetting composition is to be destabilized, or broken, for purposes of forming the stratified wetting composition in the wet wipe of the present invention. Exemplary anionic emulsifiers include sodium stearate and triethanolamine stearate. An exemplary cationic emulsifier is behentrimonium chloride. Exemplary polymeric emulsifiers include those available under the tradenames PEMULEN™ and SEPIGEL™. Zwitterionic, amphoteric, or nonionic emulsifiers may also be appropriate in some embodiments.

The concentration of the emulsifier in the emulsified wetting composition may vary depending upon a number of factors, including for example the type and concentration of other components in the composition, as well as the type of emulsifier being used and/or the way in which the emulsified wetting composition is to be destabilized, or broken, for purpose of forming the stratified wetting composition in the wet wipe of the present invention. Typically, however, the concentration of the emulsifier in the emulsified wetting composition may be greater than about 0.05 weight percent, greater than about 0.1 weight percent, greater than about 0.25 weight percent, greater than about 0.5 weight percent, greater than about 1 weight percent or more (e.g., greater than about 1.5 weight percent, about 2 weight percent, etc.). In these or other embodiments, the concentration of the emulsifier in the emulsified wetting composition may be less than about 10 weight percent, less than about 8 weight percent, less than about 6 weight percent, or less than about 5 weight percent. For example, the concentration of the emulsifier in the emulsified wetting composition may be in the range of between about 0.05 weight percent and less than about 10 weight percent, or between about 0.2 and about 8 weight percent, or between about 0.5 and about 6 weight percent, or between about 1 and about 5 weight percent. In one particular embodiment, the emulsified wetting composition may contain a polymeric emulsifier, the concentration therein being between about 0.05 weight percent and about 4 weight percent, or about 0.05 weight percent and about 3 weight percent, or about 0.1 weight percent and about 2 weight percent.

In addition to the emulsifier, the oil phase, or discontinuous phase, of the emulsified wetting composition may include a number of different components (as further detailed herein below), depending upon for example the effect to be imparted on the skin by use of a wipe comprising the wetting composition, and/or the type and/or concentration of the other components present in the oil phase and/or the continuous water phase. For example, in some embodiments the oil phase may comprise a polydimethyl-siloxane, an organo-modified polydimethyl siloxane, a silicone gum/resin/fluid, and/or a short-chain carbon ester. Such additives or components may be used, for example, to impart a light, silky feel to the skin. Alternatively, however, the oil phase may optionally contain emollients in any form, and/or contain various silicones, silicone derivatives, natural oils, synthetic oils, esters, fatty alcohols, waxes, thickeners, active ingredients, sunscreens, preservatives, dyes, fragrances, etc. Among the exemplary ester compounds are included isononyl isononanoate, cetyl ethylhexanoate, octyldodecyl neopentanoate, isodecyl neopentanoate, isocetyl ethylhexanoate, neopenthyl glycol diheptanoate, etc.

C. Optional Wipe/Wetting Composition Components

In addition to water and one or more of the other components noted above, the aqueous, or continuous, phase, and/or the oil, or discontinuous, phase, may optionally contain one or more additional components (as further detailed herein below), such as for example a preservative, a chelating agent, a thickener, a botanical, a humectant, a sunscreen, a pH modifier, a suspending agent, etc., and/or an active ingredient of some kind, or some combination thereof. (See, e.g., the list of potential skin care components or actives listed in U.S. Pat. No. 6,338,855, the entire content of which is incorporated herein by reference for all relevant purposes, to the extent it is consistent with the present invention.)

It is to be noted that the selection from among these components for the oil discontinuous phase, the water continuous phase, and the emulsifier, as well as the concentrations thereof, and/or the ratio of the oil phase to the aqueous phase (or alternatively the percent of the emulsified wetting composition attributable to the oil phase and/or to the aqueous phase), may be done using means known in the art. For example, the various components used, as well as the respective concentrations thereof, may be determined using means generally known in the art, in order to optimize the viscosity of the wetting composition, the stability of the emulsion of the wetting composition, the ability of the wetting composition to phase separate and/or the timing of phase separation, and/or the feel (or other aspect) imparted by the final wet wipe product.

It is to be further noted that the concentration of the oil phase in the oil-in-water emulsion, or emulsified oil-in-water wetting composition, may be optimized for the intended end use of the wipe. Typically, however, in at least some embodiments, the concentration of the oil phase in the emulsified wetting composition is less than 50 weight percent (e.g., less than about 45 weight percent, about 40 weight percent, about 35 weight percent, or about 30 weight percent), and greater than about 1 weight percent (e.g., greater than about 2 weight percent, about 3 weight percent, about 5 weight percent, or about 10 weight percent), based on the total weight of the emulsified wetting composition. For example, in some embodiments the concentration of the oil phase in the emulsified wetting composition may be in the range of between about 1 and less than 50 weight percent, about 2 and about 45 weight percent, about 3 and about 40 weight percent, about 5 and about 35 weight percent, or about 6 and about 30 weight percent. Similarly, the concentration of the aqueous phase in the oil-in-water emulsion, or emulsified oil-in-water wetting composition, may be optimized for the intended end use of the wipe. Typically, however, the concentration of the aqueous phase in the emulsified wetting composition is greater than 50 weight percent (e.g., greater than about 55 weight percent, about 60 weight percent, about 65 weight percent, or about 70 weight percent), and is less than about 100 weight percent (e.g., less than about 98 weight percent, about 97 weight percent, about 95 weight percent, or about 90 weight percent), based on the total weight of the emulsified wetting composition. For example, in some embodiments the concentration of the aqueous phase in the emulsified wetting composition may be in the range of between greater than 50 weight percent and less than about 100 weight percent, about 55 and about 98 weight percent, about 60 and about 97 weight percent, about 65 and about 95 weight percent, or about 70 and about 90 weight percent. Stated another way, the weight ratio of the aqueous phase to the oil phase in the emulsified wetting composition may be between greater than about 1:1 and less than about 100:1, or greater than about 1.5:1 and about 50:1, or greater than about 2:1 and less than about 20:1, the ratio for example being about 3:1, about 5:1, or about 10:1.

1. Skin-Care Additives

As used herein, the term "skin-care additives" represents additives, which provide one or more benefits to the user, such as a reduction in the probability of having diaper rash and/or other skin damage caused by fecal enzymes. These enzymes, particularly trypsin, chymotrypsin and elastase, are proteolytic enzymes produced in the gastrointestinal tract to digest food. In infants, for example, the feces tend to be watery and contain, among other materials, bacteria, and some amounts of undegraded digestive enzymes. These enzymes, if they remain in contact with the skin for any appreciable period of time, have been found to cause an irritation that is uncomfortable in itself and can predispose the skin to infection by microorganisms. As a countermeasure, skin-care additives may include, but are not limited to, the enzyme inhibitors and sequestrants set forth hereafter.

The concentration of the skin-care additive in the wetting composition may be optimized for a given use, or application of the wipe, using means known in the art. Typically, however, the concentration of the skin-care additive in the wetting composition is less than about 5 weight percent, about 4 weight percent, about 2 weight percent, or even about 1 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.06 weight percent of a skin-care additive.

A variety of skin-care additives may be added to the wetting composition and the water-disintegratable wipe of the present invention. For example, in one embodiment, skin-care additives in the form of particles may be added to serve as fecal enzyme inhibitors, offering potential benefits in the reduction of diaper rash and skin damage caused by fecal enzymes. Another example is provided in U.S. Pat. No. 6,051,749, which discloses organophilic clays in a woven or nonwoven web, which are said to be useful for inhibiting fecal enzymes. Such materials may be used in the present invention, including reaction products of a long chain organic quaternary ammonium compound with one or more of the following clays: montmorillonite, bentonite, beidellite, hectorite, saponite, and stevensite.

Other known enzyme inhibitors and sequestrants may be used as skin-care additives in the wetting composition of the present invention, including those that inhibit trypsin and other digestive or fecal enzymes, and inhibitors for urease. For example, enzyme inhibitors and anti-microbial agents may be used to prevent the formation of odors in body fluids. For example, urease inhibitors, which are also said to play a role in odor absorption, are disclosed by T. Trinh in PCT Pat. Application No. 98/26808. Such inhibitors may be incorporated into the wetting composition and the water-disintegratable wipes of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride.

Other salts that have been disclosed as having urease inhibition properties include ferric and aluminum salts, especially the nitrates, and bismuth salts. Other urease inhibitors are disclosed by T. Trinh, including: hydroxamic acid and its derivatives; thiourea; hydroxylamine; salts of phytic acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosphoramidates without substitution on the nitrogen; boric acid and/or its salts, including especially, borax, and/or organic boron acid compounds; the compounds disclosed in European Patent Application No. 408,199; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; phenic acid; N,N-dihalo-2-imidazolidinones; N-halo-2-oxazolidinones; thio- and/or acyl-phosphorylamide and/or substituted derivatives thereof, thiopyridine-N-oxides, thiopyridines, and thiopyrimidines; oxidized sulfur derivatives of diaminophosphinyl compounds; cyclotriphosphazatriene derivatives; ortho-diaminophosphinyl derivatives of oximes; bromo-nitro compounds; S-aryl and/or alkyl diamidophosphorothiolates; diaminophosphinyl derivatives; mono- and/or polyphosphorodiamide; 5-substituted-benzoxathiol-2-ones; N(diaminophosphinyl)-arylcarboxamides; alkoxy-1,2-benzothaizin compounds; as well as other compounds generally known in the art.

As further detailed elsewhere herein, many other skin-care additives may be incorporated into the wetting composition and pre-moistened wipes of the present invention, including, but not limited to, sun blocking agents and UV absorbers, acne treatments, skin protectants (e.g., allantoin, calamine, cocoa butter, colloidal oatmeal, dimethicone, glycerin, kaolin, lanolin, mineral oil, petrolatum, topical starch, white petrolatum, and zinc oxide), pharmaceuticals, baking soda (including encapsulated forms thereof), vitamins and their derivatives such as Vitamins A or E, botanicals such as witch hazel extract and aloe vera, allantoin, emollients, disinfectants, hydroxy acids for wrinkle control or anti-aging effects, tanning promoters, skin lighteners, deodorants and antiperspirants, ceramides for skin benefits and other uses, astringents, moisturizers, nail polish removers, insect repellents, antioxidants, antiseptics, anti-inflammatory agents and the like, provided that the additives are compatible with (when present) an ion-sensitive or water-dispersible binder composition associated therewith (i.e., they do not cause a substantial loss of strength in the wet state of the pre-moistened wipes, prior to dilution in water, while permitting dispersibility in water), as well as the other components of the emulsified wetting composition (e.g., additives which do not interfere with the stability of the emulsion or result in premature phase separation therein).

Other useful materials for skin care and other benefits are listed in McCutcheon's 1999, Vol. 2: Functional Materials, MC Publishing Company, Glen Rock, N.J. Many useful botanicals for skin care are provided by Active Organics, Lewisville, Tex.

2. Odor Control Additives

Suitable odor control additives for use in the wetting composition and pre-moistened wipes of the present invention include, but are not limited to, zinc salts; talc powder; encapsulated perfumes (including microcapsules, macrocapsules, and perfume encapsulated in liposomes, vessicles, or microemulsions); chelants, such as ethylenediamine tetra-acetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites (e.g., those of BF Technologies, located in Beverly, Mass., sold under the trademark HEALTHSHIELD™, and AgIONT™ antimicrobial compound sold by AgION Technologies, located in Wakefield, Mass.); triclosan; kieselguhr; and/or mixtures thereof. In addition to controlling odor from the body or body wastes, odor control strategies can also be employed to mask or control any odor of the treated substrate.

The concentration of the odor control additive in the wetting composition may be optimized for a given use, or application of the wipe, using means known in the art. Typically, however, the concentration of the odor control additive in the wetting composition is less than about 5 weight percent, about 4 weight percent, about 2 weight percent, or even about 1 weight percent, based on the total weight of the wetting composition. For example, in various embodiments the wetting composition may contain from about 0.01 weight percent to about 2 weight percent, or from about 0.03 weight percent to about 1 weight percent, or from about 0.05 weight percent to about 0.5 weight percent of an odor control additive.

In one embodiment of the present invention, the wetting composition and/or water-disintegratable wipe comprise derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product.

Principles for the application of chitosan or chitin derivatives to nonwoven webs and cellulosic fibers are described by S. Lee et al. in "Antimicrobial and Blood Repellent Finishes for Cotton and Nonwoven Fabrics Based on Chitosan and Fluoropolymers," Textile Research Journal, 69(2); 104-112, February 1999.

3. Detackifying Agents

While elevated salt concentrations may reduce the tack of the triggerable binder, other means of tack reduction are often desirable. Thus, detackifying agents may be used in the wetting composition to reduce the tackiness, if any, of the triggerable binder. Suitable detackifiers include any substance known in the art to reduce tack between two adjacent fibrous sheets treated with an adhesive-like binder composition (e.g., polymer binder) or any substance capable of reducing the tacky feel of an adhesive-like binder on the skin, reducing product peel force, or reduce dispensing force.

Detackifiers may be applied as solid particles in dry form, as a suspension or as a slurry of particles. Deposition may be by spray, coating, electrostatic deposition, impingement, filtration (i.e., a pressure differential drives a particle-laden gas phase through the substrate, depositing particles by a filtration mechanism), and the like, and may be applied uniformly on one or more surfaces of the substrate or may be applied in a pattern (e.g., repeating or random patterns) over a portion of the surface or surfaces of the substrate. The detackifier may be present throughout the thickness of the substrate, or it may be concentrated at one or both surfaces, and may be substantially only present on one or both surfaces of the substrate.

Specific detackifiers include, but are not limited to, powders, such as talc powder, calcium carbonate, mica; starches, such as corn starch; lycopodium powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins and thermoplastics, waxes, debonding agents known in the paper industry including compounds having alkyl side chains such as those having 16 or more carbons, and the like. Compounds used as release agents for molds and candle making, as well as dry lubricants and fluorinated release agents, may also be considered.

In one embodiment, the detackifier comprises polytetrafluoroethylene (PTFE), such as PTFE telomer (KRYTOX® DF) compound, used in the PTFE release agent dry lubricant MS-122DF (marketed by Miller-Stephenson of Danbury, Conn.) as a spray product.

The concentration of the detackifying agent in the wetting composition may be optimized for a given use, or application of the wipe, using means known in the art. Typically, however, the concentration of the detackifying agent in the wetting composition is less than about 25 weight percent, about 15 weight percent, about 10 weight percent, or even about 5 weight percent, based on the total weight of the wetting composition. For example, in various embodiments the wetting composition may contain from about 0.01 weight percent to about 10 weight percent, or from about 0.02 weight percent to about 5 weight percent, or from about 0.05 weight percent to about 2 weight percent of a detackifying agent.

In addition to acting as a detackifying agent, starch compounds may also improve the strength properties of the pre-moistened wipes. For example, ungelled starch particles, such as hydrophilic tapioca starch, when present at a level of for example about 1% or higher by weight relative to the weight of the wetting composition, may permit the, for example, ion-triggerable, water-disintegratable wipe to maintain the same strength at a lower salt concentration than is possible without the presence of starch. Thus, for example, a given strength may be achieved with about 2% salt in the wetting composition in the presence of starch compared to a level of about 4% salt without starch. Starch may be applied, for example, by adding the starch to a suspension of laponite to improve the dispersion of the starch within the wetting composition.

4. Microparticulates

The wetting composition of the present invention may be further modified by the addition of solid particulates or microparticulates. Suitable particulates include, but are not limited to, mica, silica, alumina, calcium carbonate, kaolin, talc, zinc oxide, titanium dioxide, zeolites, tapioca starch, corn starch, potato starch, tapioca starch, rice starch, root starch, pea starch, sweet potato starch, amaranth, banana starch, sorghum, barley flour, wheat flour, oat starch, rye starch, modified starches (such as starch octenylsuccinate, hydroxypropylated di-starch phosphates, and thermally inhibited starch), oatmeal, treated titanium dioxide, treated zinc oxide, iron oxide, treated iron oxide, boron nitride, fluorocarbon powder, polytetrafluoro-ethylene powder, chlorotrifluoro-ethylene-ethylene powder, cellulose propionate powder, cellulose acetate butyrate powder, cellulose acetate, spray-dried vegetable oil, shea butter powder, methylpentene polymer powder, ethyl cellulose powder, acetal homopolymer powder, acrylic polymer powder, cellulose nitrate powder, polypropylene powder, polyallomer powder, polybutylene powder, inonmer polymer powder, polyethylene powder, nylon powder, polyamide powder, acrylics multipolymer powder, styrene butadiene thermoplastic powder, polyvinylchloride powder, nylon (polyamide) powder, urea formaldehyde powder, styrene acrylonitrile copolymer, polystyrene powder, polycarbonate, polysulfone powder, non-swellable natural and/or synthetic clays, kaolin, mica, sulfur, organically modified clays, non-solublized silicone resin powder, non-solublized PEG-12 dimethicone crosspolymer powder, non-solublized dimethicone crosspolymer powder, non-solublized divinyldimethicone/dimethicone copolymer, mixtures thereof, and the like. The powders may be presented in the form of microcapsules, and the like.

The particulates may be treated with stearic acid or other additives to enhance the attraction or bridging of the particulates to the binder system, if desired. Also, two-component microparticulate systems, commonly used as retention aids in the papermaking industry, may also be used. Such two-component microparticulate systems generally comprise a colloidal particle phase, such as silica particles, and a water-soluble cationic polymer for bridging the particles to the fibers of the web to be formed. The presence of particulates in the wetting composition can serve one or more useful functions, such as (1) increasing the opacity of the water-disintegratable wipe; (2) modifying the rheology or reducing the tackiness of the wipe; (3) improving the tactile properties of the wipe; or (4) delivering desired agents to the skin via a particulate carrier, such as a porous carrier or a microcapsule.

The concentration of the microparticulate additive in the wetting composition may be optimized for a given use, or application of the wipe, using means known in the art. Typically, however, the concentration of the microparticulate additive in the wetting composition is less than about 25 weight percent, about 15 weight percent, about 10 weight percent, or even about 5 weight percent, based on the total weight of the wetting composition. For example, in various embodiments the wetting composition may contain from about 0.05 weight percent to about 10 weight percent, or from about 0.1 weight percent to about 5 weight percent, or from about 0.5 weight percent to about 2.5 weight percent of a microparticulate additive.

5. Microcapsules and Other Delivery Vehicles

Microcapsules and other delivery vehicles may also be used in the wetting composition of the present invention to provide, for example: skin-care agents; medications; comfort promoting agents, such as eucalyptus; perfumes; odor control additives; vitamins; powders; and other additives to the skin of the user. The concentration of the microcapsules (or other delivery vehicle) in the wetting composition may be optimized for a given use, or application of the wipe, using means known in the art. Typically, however, the concentration of the microcapsules (or other delivery vehicle) in the wetting composition is less than about 25 weight percent, about 15 weight percent, about 10 weight percent, or even about 5 weight percent, based on the total weight of the wetting composition. For example, in various embodiments the wetting composition may contain from about 0.05 weight percent to about 10 weight percent, or from about 0.2 weight percent to about 5 weight percent, or from about 0.5 weight percent to about 2.5 weight percent of the microcapsules (or other delivery vehicle).

Microcapsules and other delivery vehicles are well known in the art. For example, POLY-PORE® E200 (Chemdal Corp., Arlington Heights, Ill.), is a delivery agent comprising soft, hollow spheres that can contain an additive at over 10 times the weight of the delivery vehicle. Additives reported to have been used with POLY-POREO E200 include, but are not limited to, benzoyl peroxide, salicylic acid, retinol, retinyl palmitate, octyl methoxycinnamate, tocopherol, silicone compounds (DC 435), and mineral oil. Another useful delivery vehicle is a sponge-like material marketed as POLY-POREO L200, which is reported to have been used with silicone (DC 435) and mineral oil. Other known delivery systems include cyclodextrins and their derivatives, liposomes, polymeric sponges, and spray-dried starch.

Additives present in microcapsules are isolated from the environment and the other agents in the wetting composition until the wipe is applied to the skin, whereupon the microcapsules break and deliver their load to the skin or other surfaces.

6. Preservatives and Anti-Microbial Agents

The wetting composition of the present invention may also contain preservatives and/or anti-microbial agents. Suitable preservatives and anti-microbial agents include, but are not limited to, DMDM hydantoin, iodopropynyl butylcarbamate, Kathon (Rohm and Hass, Philadelphia, Pa.), methylparaben, propylparaben, 2-bromo-2-nitropropane-1,3-diol, benzoic acid, benzalkonium chloride, benzethonium chloride, sodium hydroxymethylglycinate, diazolidinyl urea, phenoxyethanol, acrolein/acrylic acid copolymer, alpinia uraiensis stalk/leaf water, ammonium benzoate, ammonium propionate, ammonium silver zinc aluminum silicate, benzisothiazolinone, benzoic acid, benzylhemiformal, benzylparaben, butyl benzoate, butylparaben, citrus grandis (grapefruit) fruit extract, galla rhois gallnut extract, sodium benzoate, sodium pyrithione, sorbic acid, and the like.

The concentration of the preservative and/or anti-microbial agent in the wetting composition may be optimized for a given use, or application of the wipe, using means known in the art. Typically, however, the concentration of the preservative and/or anti-microbial agent in the wetting composition is less than about 2 weight percent (on an active basis), about 1.5 weight percent, about 1 weight percent, or even about 0.5 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.5 weight percent of a preservative and/or anti-microbial agent.

7. Pharmaceutical or Treatment Agent

The wetting composition may also contain one or more pharmaceutical or treatment agents. Suitable pharmaceutical or treatment agents for use in the wetting composition of the present invention include, for example, hormones, antibiotics, anesthetics, analgesics, immunodilators, contraceptives, and the like. The concentration of the agents in the wetting composition may be optimized for a given use, or application of the wipe, using means known in the art.

8. Emollients

Emollient additives or components may be used in the oil (discontinuous) phase, and/or in the aqueous (continuous) phase, in accordance with the present disclosure, for example, to impart a light, silky feel to the skin. Suitable emollients include, but are not limited to, PEG 75 lanolin, methyl gluceth 20 benzoate, C12-C15 alkyl benzoate, ethoxylated cetyl stearyl alcohol, products marketed as Lambent wax WS-L, Lambent WD-F, Glucam P20 (Amerchol), Polyox WSR N-10 (Union Carbide), Polyox WSR N-3000 (Union Carbide), Luviquat (BASF), Finsolv SLB 101 (Finetex Corp.), mink oil, stearyl alcohol, Estol 1517 (Unichema), and Finsolv SLB 201 (Finetex Corp.).

The emollient composition may optionally comprise a plastic or fluid emollient, such as one or more liquid hydrocarbons (e.g., petrolatum), mineral oil and the like, vegetable and animal fats (e.g., lanolin, phospholipids and their derivatives) and/or a silicone material, such as one or more alkyl-substituted polysiloxane polymers, including the polysiloxane emollients disclosed in U.S. Pat. No. 5,891,126. For example, in one embodiment, it is possible that a liquid hydrocarbon emollient and/or alkyl-substituted polysiloxane polymer may be blended or combined with one or more fatty acid ester emollients derived from fatty acids or fatty alcohols. In this or an alternative embodiment, the emollient material may be in the form of an emollient blend which comprises a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. Desirably, the emollient blend may comprise a combination of liquid hydrocarbons (e.g., petrolatum) with dimethicone or with dimethicone and other alkyl substituted polysiloxane polymers. In some other embodiments of the present invention, it is contemplated that blends of liquid hydrocarbon emollients and/or alkyl-substituted polysiloxane polymers may be blended with one or more fatty acid ester emollients derived from fatty acids or fatty alcohols. PEG-7 glyceryl cocoate, available as Standamul HE (Henkel Corp., Hoboken, N.J.), may also be considered.

In these or other embodiments, the oil (or lipid) phase may additionally, or alternatively, comprise components suitable for the formulation of a lotion. For example, the oil phase may include various components, such as for example, natural and/or synthetic fats or oils, silicones, polyethylene glycol, polyols, ethoxylated glycols, esters, glycerin, fatty alcohols, waxes, hydrogenated hydrocarbons solubilizers, moisturizers, cleaning agents, other emollients, and/or the like.

The term "natural fat or oil" is intended to include fats, oils, essential oils, essential fatty acids, non-essential fatty acids, phospholipids, and combinations thereof. Suitable fats and oils include Apricot Kernel Oil, Avocado Oil, Babassu Oil, Borage Seed Oil, Butter, C12-C18 Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Chemy Pit Oil, Chia Oil, Cocoa Butter, Coconut Oil, Cod Liver Oil, Corn Germ Oil, Corn Oil, Cottonseed Oil, C10-C18 Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated C12-C18 Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, oil extracts of various other botanicals, and other vegetable or partially hydrogenated vegetable oils, and the like, as well as mixtures thereof.

Suitable fatty acids include Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Suitable essential oils include Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

Some preferred natural fats and oils include, but are not limited to Avocado Oil, Apricot Oil, Babassu Oil, Borage Oil, Camellia oil, Canola oil, Castor Oil, Coconut oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Phospholipids, Rapeseed Oil, Palmitic Acid, Stearic Acid, Linoleic Acid, Rose Hip Oil, Sunflower Oil, Soybean Oil, PROLIPID 141 (proprietary blend of Glyceryl Stearate, Fatty Acids, Lecithin, and Phospholipids from International Specialty Products, Wayne, N.J.) and the like, as well as mixtures thereof.

The term "synthetic fat or oil" is intended to include synthetic fats and oils, esters, silicones, other emollients, and combinations thereof. Examples of suitable synthetic fats or oils include petrolatum and petrolatum based oils, mineral oils, mineral jelly, isoparaffins, polydimethylsiloxanes such as methicone, cyclomethicone, dimethicone, dimethiconol, trimethicone, alkyl dimethicones, alkyl methicones, alkyldimethicone copolyols, organo-siloxanes (i.e., where the organic functionality can be selected from alkyl, phenyl, amine, polyethylene glycol, amine-glycol, alkylaryl, carboxal, and the like), silicones such as silicone elastomer, phenyl silicones, alkyl trimethylsilanes, dimethicone crosspolymers, cyclomethicone, gums, resins, fatty acid esters (esters of $C_6$-$C_{28}$ fatty acids and C6-C28 fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, propylene glycol esters and derivatives, alkoxylated carboxylic acids, alkoxylated alcohols, fatty alcohols, Guerbet alcohols, Guerbet Acids, Guerbet Esters, and other cosmetically acceptable emollients.

Examples of suitable esters include, but are not limited to, cetyl palmitate, stearyl palmitate, cetyl stearate, isopropyl laurate, isopropyl myristate, isopropyl palmitate, isononyl isononanoate, cetyl ethylhexanoate, octyldodecyl neopentanoate, isodecyl neopentanoate, isocetyl ethylhexanoate, neopenthyl glycol diheptanoate, etc., and combinations thereof.

Water-soluble, self-emulsifying emollient oils may also be useful in the present wetting compositions, including for example the polyoxyalkoxylated lanolins and the polyoxyalkoxylated fatty alcohols, as disclosed in U.S. Pat. No. 4,690,821. The polyoxyalkoxy chains may comprise mixed propylenoxy and ethyleneoxy units. The lanolin derivatives may typically comprise about 20-70 such lower-alkoxy units, while the C12-C20 fatty alcohols may be derivatized with about 8-15 lower-alkyl units. One such useful lanolin derivative is Lanexol AWS (PPG-12-PEG-50, Croda, Inc., New York, N.Y.). A useful poly(15-20)C2-C3-alkoxylate is PPG-5-Ceteth-20, known as Procetyl AWS (Croda, Inc.).

According to one embodiment of the present invention, the emollient material reduces undesirable tactile attributes, if any, of the wetting composition. For example, emollient materials, including dimethicone, can reduce the level of tackiness that may be caused by the ion-sensitive binder or other components in the wetting composition, thus serving as a detackifier.

The concentration of the emollient in the wetting composition may be optimized for a given use, or application of the wipe, using means known in the art. Typically, however, the concentration of the emollient in the wetting composition is less than about 25 weight percent, about 15 weight percent, about 5 weight percent, or even about 2 weight percent, based on the total weight of the wetting composition. For example, in various embodiments the wetting composition may contain from about 0.01 weight percent to about 10 weight percent, or from about 0.1 weight percent to about 5 weight percent, or from about 0.2 weight percent to about 2 weight percent of an emollient.

In one embodiment, the wipe of the present invention comprises an oil-in-water emulsified wetting composition that comprising an oil phase containing at least one emollient oil and at least one emollient wax stabilizer dispersed in an aqueous phase comprising at least one polyhydric alcohol emollient and at least one organic water-soluble detergent, as disclosed for example in U.S. Pat. No. 4,559,157.

9. Surface Feel Modifiers

Surface feel modifiers are used to improve the tactile sensation (e.g., lubricity) of the skin during use of the product. Suitable surface feel modifiers include, but are not limited to commercial debonders and softeners, such as the softeners used in the art of tissue making (including quaternary ammonium compounds with fatty acid side groups, silicones, waxes, and the like). Exemplary quaternary ammonium compounds with utility as softeners are disclosed in, for example, U.S. Pat. Nos. 3,554,862; 4,144,122; 5,573,637; and U.S. Pat. No. 4,476,323.

The concentration of the surface feel modifier in the wetting composition may be optimized for a given use, or application of the wipe, using means known in the art. Typically, however, the concentration of the surface feel modifier in the wetting composition is less than about 2 weight percent, about 1.5 weight percent, about 1 weight percent, or even about 0.5 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.1 weight percent of a preservative and/or anti-microbial agent.

10. Fragrances and Fragrance Solublizers

A variety of fragrances may be used in the wetting composition of the present invention. The concentration of thereof in the wetting composition may be optimized for a given use, or application of the wipe, using means known in the art. Typically, however, the concentration of the fragrance in the wetting composition is less than about 2 weight percent, about 1.5 weight percent, about 1 weight percent, or even about 0.5 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.1 weight percent of a fragrance.

Further, a variety of fragrance solublizers may be used in the wetting composition of the present invention. Suitable fragrance solublizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), Brij 78 and Brij 98 (ICI Surfactants), Arlasolve 200 (ICI Surfactants), Calfax 16L-35 (Pilot Chemical Co.), Capmul POE-S (Abitec Corp.), Finsolv SUBSTANTIAL (Finetex), and the like.

The concentration of the fragrance solublizer in the wetting composition may be optimized for a given use, or application of the wipe, using means known in the art. Typically, however, the concentration of the fragrance solublizer in the wetting composition is less than about 2 weight percent, about 1.5 weight percent, about 1 weight percent, or even about 0.5 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.1 weight percent of a fragrance solublizer.

11. Opacifiers

Suitable opacifiers include, but are not limited to, titanium dioxide or other minerals or pigments, and synthetic opacifiers, such as REACTOPAQUE® particles (available from Sequa Chemicals, Inc., Chester, S.C.). The concentration of the opacifier in the wetting composition may be optimized for a given use, or application of the wipe, using means known in the art. Typically, however, the concentration of the opacifier in the wetting composition is less than about 2 weight percent, about 1.5 weight percent, about 1 weight percent, or even about 0.5 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.1 weight percent of an opacifier.

12. pH and pH Control Agents

The wetting composition of the present invention may optionally contain a pH modifying or control agent. Suitable pH agents for use in the wetting composition include, but are not limited to, malic acid, citric acid, hydrochloric acid, acetic acid, sodium hydroxide, potassium hydroxide, and the like. An appropriate pH range minimizes the amount of skin irritation resulting from the wetting composition on the skin. Also, pH controls can be used to destabilize the emulsion, as further detailed herein.

The concentration of the pH agent in the wetting composition, and/or the pH of the wetting composition itself, may be optimized for a given application. For example, in some embodiments the pH of the wetting composition, prior to or after the addition of a pH agent (i.e., without or without a pH agent, given that a pH agent may not be needed in every instance) may be greater than about 3.5, the pH for example being about 4, about 4.5, about 5, about 5.5, about 6, or even about 6.5. For example, in various embodiments the pH of the wetting composition may be in the range of from about 3.5 to about 6.5, or from about 4 to about 5, or from about 4.5 to about 5.5. Similarly, the overall pH of the wet wipe product (i.e., the complete wet wipe product, including the fabric portion and the wetting solution portion), may in some embodiments be in the range of from about 3.5 to about 6.5, or from about 4 to about 6, or from about 4.5 to about 5.5, or from about 4.75 to about 5.25.

The concentration of the pH agent in the wetting composition, when present, may be optimized for a given use, or application of the wipe, and/or the desired pH of the wetting composition or wipe itself, using means known in the art. Typically, however, when used, the concentration of the pH agent in the wetting composition is less than about 2 weight percent, about 1.5 weight percent, about 1 weight percent, or even about 0.5 weight percent, based on the total weight of the wetting composition. For example, in various embodiments the wetting composition may contain from about 0.01 weight percent to about 2 weight percent, or from about 0.02 weight percent to about 1 weight percent, or from about 0.03 weight percent to about 0.1 weight percent of a pH agent.

In this regard it is to be noted, however, that in one embodiment of the present invention, the pH of the emulsified wetting composition is adjusted as needed, as determined by means known in the art, in order to destabilize it, either prior to or after the composition contacts the fibrous substrate of the wipe. Accordingly, it is to be understood that the above-noted pH ranges and/or concentrations may be for the emulsion prior to, or after, being treated in order to destabilize it. For example, in one embodiment, the emulsified wetting composition may be prepared as necessary (e.g., with or without a pH control agent) to be stable and have a pH of about 7. After being prepared, a pH control agent may be added in order to lower the pH to about 4, which is sufficiently high to render the emulsion semi-stable. The semi-stable emulsified wetting composition may then be applied to the fibrous substrate, the wetting composition then stratifying (i.e., phase separating) some time (e.g., about 3 hours) after being applied to the fibrous substrate.

13. Wetting Agents

A variety of wetting agents and/or cleaning agents may be used in the wetting composition of the present invention. Suitable wetting agents and/or cleaning agents include, but are not limited to, detergents and nonionic, amphoteric, cationic, and anionic surfactants. The wetting composition may contain less than about 3 weight percent of wetting agents and/or cleaning agents, based on the total weight of the wetting composition. Alternatively, the wetting composition may contain from about 0.01 weight percent to about 2 weight percent of wetting agents and/or cleaning agents, or from about 0.1 weight percent to about 0.5 weight percent of wetting agents and/or cleaning agents. Suitable cationic surfactants may include, but are not limited to, quaternary ammonium alkyl halides like cetyl trimethyl ammonium chloride and cetyl trimethyl ammonium bromide.

Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants. One function of the surfactant is to improve wetting of the dry substrate with the wetting composition. Another function of the surfactant can be to disperse bathroom soils when the pre-moistened wipe contacts a soiled area and to enhance their absorption into the substrate. The surfactant can further assist in make-up removal, general personal cleansing, hard surface cleansing, odor control, and the like. One commercial example of an amino-acid based surfactant is acylglutamate, marketed under the Amisoft™ name (by Ajinomoto Corp., Tokyo, Japan).

Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic™ surfactants (BASF Wyandotte Corp.), especially those in which the polyoxypropylene ether has a molecular weight of about 1500-3000 and the polyoxyethylene content is about 35-55% of the molecule by weight (i.e. Pluronic™ L-62).

Other useful nonionic surfactants include, but are not limited to, the condensation products of C8-C22 alkyl alcohols with 2-50 moles of ethylene oxide per mole of alcohol.

Examples of compounds of this type include the condensation products of C11-C15 secondary alkyl alcohols with 3-50 moles of ethylene oxide per mole of alcohol, which are commercially-available as the Poly-Tergent SLF series from Olin Chemicals or the TERGITOL® series (from Union Carbide); i.e., TERGITOL® 25-L-7, which is formed by condensing about 7 moles of ethylene oxide with a C12-C15 alkanol.

Other nonionic surfactants, which may be employed in the wetting composition of the present invention, include the ethylene oxide esters of C6-C12 alkyl phenols such as (nonylphenoxy)polyoxyethylene ether. Particularly useful are the esters prepared by condensing about 8-12 moles of ethylene oxide with nonylphenol, i.e. the IGEPAL® CO series (GAF Corp.).

Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Corning Corp as Dow Corning 190 and 193 surfactants (CTFA name: dimethicone copolyol). These surfactants function, with or without any volatile silicones used as solvents, to control foaming produced by the other surfactants, and also impart a shine to metallic, ceramic, and glass surfaces.

Anionic surfactants may also be used in the wetting compositions of the present invention. Anionic surfactants are useful due to their high detergency include anionic detergent salts having alkyl substituents of 8-22 carbon atoms such as the water-soluble higher fatty acid alkali metal soaps, e.g., sodium myristate and sodium palmitate. One particular class of anionic surfactants encompasses the water-soluble sulfated and sulfonated anionic alkali metal and alkaline earth metal detergent salts containing a hydrophobic higher alkyl moiety (typically containing from about 8-22 carbon atoms) such as salts of higher alkyl mono or polynuclear aryl sulfonates having from about 1 to 16 carbon atoms in the alkyl group, with examples available as the Bio-Soft series, i.e. Bio-Soft D-40 (Stepan Chemical Co.).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10-18 carbon atoms (e.g., sodium lauryl sulfate and sodium stearyl sulfate); sodium $C_{14}$-$C_{16}$-alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a $C_{12}$-$C_{15}$ n-alkanol; i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids; e.g., lauric acid amide of taurine; as well as numerous other anionic organic surface active agents such as sodium xylene sulfonate, sodium naphthalene sulfonate, sodium toluene sulfonate and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

D. Binder Compositions and Wipe Base Sheets

1. Binder Composition

As previously noted, a number of binder compositions generally known in the art may be employed in accordance with the present invention, particularly when an ion-triggerable, water-disintegratable wipe is to be prepared. In one preferred embodiment of an ion-triggerable, water-disintegratable wipe, however, a "triggerable" binder composition is employed, and more particularly an ion triggerable cationic polymer binder composition (such as those disclosed in, for example, U.S. Pat. No. 6,994,865, the entire contents of which is incorporated herein for all relevant purposes). A preferred cationic polymer binder is the polymerization product of a vinyl-functional cationic monomer, and one or more hydrophobic vinyl monomers, such as for example those having an alkyl side chain of up to 4 carbons in length. In a particularly preferred embodiment, the ion triggerable cationic polymer binder is the polymerization product of a random polymerization of a vinyl-functional cationic monomer, and one or more hydrophobic vinyl monomers with alkyl side chain sizes of up to 4 carbons in length. Optionally, a minor amount of another vinyl monomer with a linear or branched alkyl group of 4 carbons in length or more, an alkyl hydroxy, a polyoxyalkylene, or other functional group may be employed.

The ion triggerable cationic polymer binder composition functions as an adhesive for the fibers of the tissue, airlaid pulp, or other nonwoven webs. Additionally, it provides a sufficient in-use strength (e.g., typically greater than about 300 g/in.) when in the presence of the salt-contain emulsified wetting composition detailed elsewhere herein. As previously noted, the binder composition is water-soluble or water-dispersible, when contacted with an amount of water that is sufficient to dilute the salt concentration in the wetting composition to a sufficient degree. As a result, the fibers of, for example, the nonwoven web that is treated with the binder composition are also dispersible in water, including for example tap water (e.g., hard water having for example, a concentration of about 200 ppm, 300 ppm, 400 ppm, 500 ppm or more, of metal ions, such as calcium and/or magnesium ions). For example, nonwoven webs of fibers treated with such a binder composition typically lose most of their wet strength (e.g., a strength of between about 30 and about 75 g/in.) in about 24 hours, or less.

A general structure for an ion triggerable cationic polymer suitable for use in accordance with the present invention is shown below:

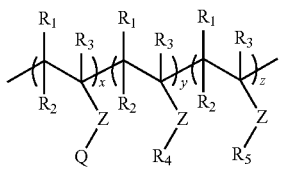

wherein: x is equal to about 1 to about 15 mole percent; y is equal to about 60 to about 99 mole percent; z is equal to 0 to about 30 mole percent; Q is selected from $C_1$ to $C_4$ alkyl ammonium, quaternary $C_1$ to $C_4$ alkyl ammonium and benzyl ammonium; Z is selected from —O—, —COO—, —OOC—, —CONH—, and —NHCO—; $R_1$, $R_2$, $R_3$ are each independently selected from hydrogen and methyl; $R_4$ is selected from methyl and ethyl; and $R_5$ is selected from hydrogen, methyl, ethyl, butyl, ethylhexyl, decyl, dodecyl, hydroxyethyl, hydroxypropyl, polyoxyethylene, and polyoxypropylene. Vinyl-functional cationic monomers may desirably include, but are not limited to, [2-(acryloxy)ethyl]trimethyl ammonium chloride (ADAMQUAT); [2-(methacryloxy)ethyl]trimethyl ammonium chloride (MADQUAT); (3-acrylamidopropyl)trimethyl ammonium chloride; N,N-diallyldimethyl ammonium chloride; [2-(acryloxy)ethyl]dimethylbenzyl ammonium chloride; [2-(methacryloxy)ethyl]dimethylbenzyl ammonium chloride; [2-(acryloxy)ethyl]dimethyl ammonium chloride; and [2-(methacryloxy)ethyl]dim-ethyl ammonium chloride. Precursor monomers, such as vinylpyridine, dimethylaminoethyl acrylate, and dimethylaminoethyl methacrylate, which can be polymerized and quaternized through post-polymerization reactions are also possible. Monomers or quaternization reagents which provide different counter-ions, such as bromide, iodide, or methyl sulfate may also be useful. Other vinyl-functional cationic monomers which may be copolymerized with a hydrophobic vinyl monomer may also be useful.

Hydrophobic monomers which may be used in these ion-sensitive cationic polymers include, but are not limited to, branched or linear $C_1$ to $C_{18}$ alkyl vinyl ethers, vinyl esters, acrylamides, acrylates, and other monomers that can be copolymerized with the cationic monomer. As used herein, the monomer methyl acrylate is considered to be a hydrophobic monomer, given that it has a solubility of about 6 g/100 ml in water at 20° C.

In a particular embodiment, the binder may be the polymerization product of a cationic acrylate or methacrylate and one or more alkyl acrylates or methacrylates having the generic structure:

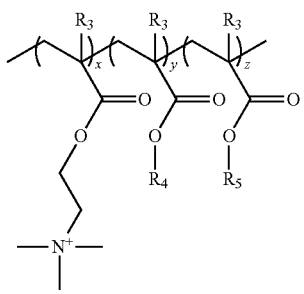

wherein: x is equal to about 1 to about 15 mole percent; y is equal to about 60 to about 99 mole percent; z is equal to 0 to about 30 mole percent; $R_3$ is as previously defined; $R_4$ is selected from methyl and ethyl; and, $R_5$ is selected from hydrogen, methyl, ethyl, butyl, ethylhexyl, decyl, dodecyl, hydroxyethyl, hydroxypropyl, polyoxyethylene, and polyoxypropylene.

In another embodiment, the ion triggerable polymer binder has the structure:

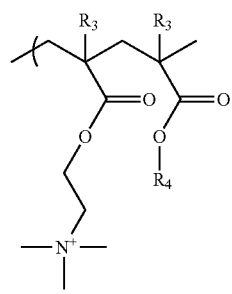

wherein: x is equal to about 1 to about 15 mole percent; y is equal to about 85 to about 99 mole percent; $R_3$ is as previously defined; and $R_4$ is $C_1$ to $C_4$ alkyl. For example, in one such particular embodiment, $R_4$ is methyl, x is equal to about 3 to about 6 mole percent; and y is equal to about 94 to about 97 mole percent.

These ion triggerable cationic polymer binders may have an average molecular weight that varies depending on, for example, the desired end use of the binder (e.g., the composition of the wipe base sheet and/or the composition of the wetting composition). Typically, however, these ion triggerable cationic polymer binders have a weight average molecular weight ranging from about 10,000 to about 5,000,000 grams per mole, or from about 25,000 to about 2,000,000 grams per mole, or from about 200,000 to about 1,000,000 grams per mole, or even from about 400,000 to about 800,000 grams per mole.

These ion triggerable cationic polymer binders may be prepared according to a variety of polymerization methods generally known in the art, including for example a solution-based polymerization method, the method and/or conditions (e.g., solvents, reaction time, reaction temperature, reagents, including polymerization initiators, etc.) being selected in order to, for example, optimize performance of the binder in the wipe of the present invention. For example, suitable solvents for such a polymerization method may include, but are not limited to, lower alcohols, such as methanol, ethanol and propanol; a mixed solvent of water and one or more of the previously mentioned lower alcohols; and a mixed solvent of water and one or more lower ketones, such as acetone or methyl ethyl ketone.

In the polymerization method, essentially any appropriate free radical polymerization initiator may be used, again in accordance with methods generally known in the art. Selection of a particular initiator may depend on a number of factors including, for example, the polymerization temperature, the solvent, and/or the monomers used. Suitable polymerization initiators include, but are not limited to, 2,2'-azobisisobutyronitrile, 2,2'-azobis(2-methylbutyro-nitrile), 2,2'-azobis(2,4-dimethylvaleronitrile), 2,2'-azobis(2-amidinopropane)dihydrochloride, 2,2'-azobis(N,N'-dimethylene-isobutylamidine), potassium persulfate, ammonium persulfate, and aqueous hydrogen peroxide. The amount of polymerization initiator may range, for example, from about 0.01 to 5 weight percent based on the total weight of monomer present, or from about 0.1 to about 4 weight percent, or from about 0.5 to about 2 weight percent.

Similarly, the polymerization temperature may vary depending on, for example, the polymerization solvent, monomers, and initiator used. Typically, however, the polymerization reaction temperature ranges from about 20° C. to about 90° C., or from about 30° C. to about 80° C. The duration of the polymerization reaction may also vary, but typically is in the range of from about 2 to about 8 hours, or from about 3 to about 7 hours.

As previously noted, the ion triggerable binder formulations remain stable and maintain their integrity while dry, or when in the presence of relatively high concentrations of monovalent and/or divalent ions, but become soluble in a quantity of water sufficient to effectively dilute the salt concentration (or the monovalent and/or divalent ion concentration). Such binder formulations may become soluble in soft water, or hard water (e.g., water having a concentration of, for example, calcium and/or magnesium ions of about 50 ppm, 100 ppm, 200 ppm, 300 ppm, 400 ppm, 500 ppm or more).

2. Co-binder Polymers

The above-noted cationic polymer binder formulations may be formed from a single triggerable cationic polymer or a combination of two or more different polymers, wherein at least one polymer is a triggerable polymer and the second is a co-binder polymer. A co-binder polymer may be of a type and in an amount such that when combined with the triggerable cationic polymer, the co-binder polymer is largely dispersed in the triggerable cationic polymer; that is, the triggerable cationic polymer is the continuous phase and the co-binder polymer is the discontinuous phase. The co-binder polymer may also meet several additional criteria. For example, the co-binder polymer may have a glass transition temperature (i.e., $T_g$) that is lower than the glass transition temperature of the ion triggerable cationic polymer. Furthermore, or alternatively, the co-binder polymer may be insoluble in water, or may reduce the shear viscosity of the ion triggerable cationic polymer.

It may be desirable, but not necessary, for the co-binder polymer, when combined with the ion triggerable cationic polymer, to reduce the shear viscosity of the ion triggerable cationic polymer to such an extent that the combination of the ion triggerable cationic polymer and the co-binder polymer is sprayable; that is, the polymer can be applied to a nonwoven fibrous substrate by spraying and the distribution of the polymer across the substrate and the penetration of the polymer into the substrate are such that the polymer formulation is uniformly applied to the substrate.

In some embodiments, the combination of the ion triggerable cationic polymer and the co-binder polymer can reduce the stiffness of the article to which it is applied, as compared for example to the article with just the ion triggerable cationic polymer is applied thereto.

The co-binder may be present at a concentration, relative to total weight of the solids of the triggerable polymer, of for example less than about 45 weight percent, about 30 weight percent, about 20 weight percent, about 15 weight percent, or about 10 weight percent. For example, in various embodiments this concentration may be in the range of from about 1 to about 45 weight percent, or from about 25 to about 35 weight percent, or alternatively from about 1 to about 20 weight percent, or from about 5 to about 25 weight percent. In this regard it is to be noted, however, that the amount of co-binder present should be low enough, for co-binders with the potential to form water insoluble bonds or films, that the co-binder remains a discontinuous phase and thus unable to create enough crosslinked, or insoluble bonds, to jeopardize the dispersibility of the treated substrate.

The co-binder polymer may have an average molecular weight that varies depending on the ultimate use of the polymer. For example, in some embodiments the co-binder polymer may have a weight average molecular weight ranging from about 500,000 to about 200,000,000 grams per mole, or from about 750,000 to about 100,000,000 grams per mole, or from about 1,000,000 to about 50,000,000 grams per mole.

The co-binder may be selected from a wide variety of polymers, as are known in the art. For example, the co-binder may be selected from the group consisting of poly(ethylene-vinyl acetate), poly(styrene-butadiene), poly(styrene-acrylic), a vinyl acrylic terpolymer, a polyester latex, an acrylic emulsion latex, poly vinyl chloride, ethylene-vinyl chloride copolymer, a carboxylated vinyl acetate latex, and the like. A variety of additional exemplary co-binder polymers are discussed in U.S. Pat. No. 6,653,406 and U.S. patent application Publication 2003/00326963.

The co-binder polymer can be in the form of an emulsion latex. The surfactant system used in such a latex emulsion is preferably one that does not substantially interfere with the dispersibility of the ion triggerable cationic polymer. Therefore, weakly anionic, nonionic, or cationic latexes may be useful. In one embodiment, the ion triggerable cationic polymer formulation comprises about 55 to about 95 weight percent ion triggerable cationic polymer and about 5 to about 45 weight percent co-binder. Alternatively, the ion triggerable cationic polymer formulation comprises about 75 weight percent ion triggerable cationic polymer and about 25 weight percent co-binder.

When a latex co-binder, or any potentially crosslinkable co-binder, is used, the latex is preferably prevented from forming substantial water-insoluble bonds that bind the fibrous substrate together and interfere with the dispersibility of the article. Thus, the latex can be free of crosslinking agents, such as N-methylol-acrylamide (NMA), or free of catalyst for the crosslinker, or both. Alternatively, an inhibitor can be added that interferes with the crosslinker or with the catalyst such that crosslinking is impaired even when the article is heated to normal crosslinking temperatures. Such inhibitors may include free radical scavengers, methyl hydroquinone, t-butylcatechol, pH control agents such as potassium hydroxide, and the like. For some latex crosslinkers, such as N-methylol-acrylamide (NMA), for example, an elevated pH (such as a pH of 8 or higher) can interfere with crosslinking at normal crosslinking temperatures (e.g., about 130° C. or higher). In an alternative approach, an article comprising a latex co-binder can be maintained at temperatures below the temperature range at which crosslinking takes place, such that the presence of a crosslinker does not lead to crosslinking, or such that the degree of crosslinking remains sufficiently low that the dispersibility of the article is not jeopardized. In yet another alternative approach, the amount of crosslinkable latex can be kept below a threshold level such that even with crosslinking, the article remains dispersible. For example, a small quantity of crosslinkable latex dispersed as discrete particles in an ion-sensitive binder can permit dispersibility even when fully crosslinked. For the later approach, the amount of latex may be below about 20 weight percent, and, more specifically, below about 15 weight percent, relative to the ion-sensitive binder.

Latex compounds, whether crosslinkable or not, need not be the co-binder. For example, SEM micrography of successful ion-sensitive binder films with useful non-crosslinking latex emulsions dispersed therein has shown that the latex co-binder particles can remain as discrete entities in the ion-sensitive binder, possibly serving in part as filler material. It is believed that other materials could serve a similar role, including a dispersed mineral or particulate filler in the triggerable binder, optionally comprising added surfactants/dispersants. For example, in one embodiment, freeflowing Ganzpearl PS-8F particles from Presperse, Inc. (Piscataway, N.J.), a styrene/divinylbenzene copolymer with about 0.4 micron particles, can be dispersed in a triggerable binder at a level of about 2 to about 10 weight percent to modify the mechanical, tactile and optical properties of the triggerable binder. Other filler-like approaches may include microparticles, microspheres, or microbeads of metal, glass, carbon, mineral, quartz, and/or plastic, such as acrylic or phenolic, and hollow particles having inert gaseous atmospheres sealed within their interiors. Examples include EXPANCEL phenolic microspheres (from Expancel of Sweden), which expand substantially when heated, or the acrylic microspheres known as PM 6545 (available from PQ Corporation of Pennsylvania). Foaming agents, including $CO_2$, dissolved in the triggerable binder could also provide helpful discontinuities as gas bubbles in the matrix of an triggerable binder, allowing the dispersed gas phase in the triggerable binder to serve as the co-binder. In general, any compatible material that is not miscible with the binder, especially one with adhesive or binding properties of its own, can be used as the co-binder, if it is not provided in a state that imparts substantial covalent bonds joining fibers in a way that interferes with the water-dispersibility of the product. However, those materials that also provide additional benefits, such as reduced spray viscosity, can be especially preferred. Adhesive co-binders, such as latex that do not contain crosslinkers or contain reduced amounts of crosslinkers, have been found to be especially helpful in providing good results over a wide range of processing conditions, including drying at elevated temperatures.

The co-binder polymer may comprise surface active compounds that improve the wettability of the substrate after application of the binder mixture. Such an approach may be helpful because wettability of a dry substrate that has been treated with a triggerable polymer binder formulation can be a problem in some embodiments, because the hydrophobic portions of the triggerable polymer formulation can become selectively oriented toward the air phase during drying, creating a hydrophobic surface that can be difficult to wet when the wetting composition is later applied, unless surfactants are added to the wetting composition. Surfactants, or other surface active ingredients, in co-binder polymers can improve the wettability of the dried substrate that has been treated with a triggerable polymer formulation. However, surfactants in the co-binder polymer are selected to avoid significant interference with the triggerable polymer formulation, and/or the stability of the emulsified wetting composition. Thus, the binder preferably maintains good integrity and tactile properties in the pre-moistened wipes with the surfactant present.

In one embodiment, an effective co-binder polymer replaces a portion of the ion triggerable polymer (e.g., cationic) formulation and permits a given strength level to be achieved in a pre-moistened wipe with at least one of lower stiffness, better tactile properties (e.g., lubricity or smoothness), or reduced cost, relative to an otherwise identical pre-moistened wipe lacking the co-binder polymer and comprising the ion triggerable cationic polymer formulation at a level sufficient to achieve the given tensile strength.

3. Other Co-binder Polymers

The Dry Emulsion Powder (DEP) binders of Wacker Polymer Systems (Burghausen, Germany) such as the VINNEK® system of binders, can be applied in some embodiments of the present invention. These are redispersible, free flowing binder powders formed from liquid emulsions. Small polymer particles from a dispersion are provided in a protective matrix of water soluble protective colloids in the form of a powder particle. The surface of the powder particle is protected against caking by platelets of mineral crystals. As a result, polymer particles that once were in a liquid dispersion are now available in a free flowing, dry powder form that can be redispersed in water or turned into swollen, tacky particles by the addition of moisture. These particles can be applied in highloft nonwovens by depositing them with the fibers during the airlaid process, and then later adding 10% to 30% moisture to cause the particles to swell and adhere to the fibers. This can be called the "chewing gum effect," meaning that the dry, non-tacky fibers in the web become sticky like chewing gum once moistened. Good adhesion to polar surfaces and other surfaces is obtained. These binders are available as free flowing particles formed from latex emulsions that have been dried and treated with agents to prevent cohesion in the dry state. They can be entrained in air and deposited with fibers during the airlaid process, or can be applied to a substrate by electrostatic means, by direct contact, by gravity feed devices, and other means. They can be applied apart from the binder, either before or after the binder has been dried. Contact with moisture, either as liquid or steam, rehydrates the latex particles and causes them to swell and to adhere to the fibers. Drying and heating to elevated temperatures (e.g., above 160° C.) causes the binder particles to become crosslinked and water resistant, but drying at lower temperatures (e.g., at 110° C. or less) can result in film formation and a degree of fiber binding without seriously impairing the water dispersibility of the pre-moistened wipes. Thus, it is believed that the commercial product can be used without reducing the amount of crosslinker by controlling the curing of the co-binder polymer, such as limiting the time and temperature of drying to provide a degree of bonding without significant crosslinking.

As reported in "New Airlaid Binders" (Nonwovens Report International, September 1999, issue 342, pp. 20-22, 28-31), dry emulsion binder powders have the advantage that they can easily be incorporated into a nonwoven or airlaid web during formation of the web, as opposed to applying the material to an existing substrate, permitting increased control over placement of the co-binder polymer. Thus, a nonwoven or airlaid web can be prepared already having dry emulsion binders therein, followed by moistening when the ion triggerable cationic polymer formulation solution is applied, whereupon the dry emulsion powder becomes tacky and contributes to binding of the substrate. Alternatively, the dry emulsion powder can be entrapped in the substrate by a filtration mechanism after the substrate has been treated with triggerable binder and dried, whereupon the dry emulsion powder is rendered tacky upon application of the wetting composition.

In another embodiment, the dry emulsion powder is dispersed into the triggerable polymer binder formulation solution either by application of the powder as the ion triggerable polymer binder formulation solution is being sprayed onto the web or by adding and dispersing the dry emulsion powder particles into the ion triggerable cationic polymer formulation solution, after which the mixture is applied to a web by spraying, by foam application methods, or by other techniques known in the art.

4. Base Sheets

The binder formulation (e.g., the ion-triggerable binder formulation detailed herein), and/or the wetting composition (e.g., the stable emulsified wetting composition, or the destabilized emulsified wetting composition) may be applied to essentially any fibrous substrate known in the art to be suitable for a wet wipe application. As previously noted, however, the binders are particularly suitable for use in ion-triggerable, water-disintegratable products. Suitable fibrous substrates include, but are not limited to, nonwoven and woven fabrics, provided the substrate is sufficient hydrophilic (i.e., provides sufficient repulsive force to the organic or oil phase of the emulsion, as phase separation occurs, in order to force that phase to migrate to or near the surface of the wipe). In many embodiments, particularly personal care products, preferred substrates are nonwoven fabrics.

In this regard it is to be noted that the fibrous substrate may comprise or be prepared from a substantial quantity of (e.g., greater than about 50 weight percent, about 60 weight percent, about 70 weight percent, about 80 weight percent, about 90 weight percent or more, based on the total weight of the substrate) a naturally hydrophilic material (e.g., cellulosic materials, such as cotton or rayon). Alternatively, however, the fibrous substrate may comprise or be prepared from hydrophobic materials that are subsequently treated in some way to render them sufficiently hydrophilic for use in the present invention. For example, in an alternative embodiment, a hydrophobic fibrous substrate, such as one prepared from or comprising a substantial quantity of polypropylene, may be surface treated, using techniques known in the art, to make the surface (or near surface region) wettable or hydrophilic.

It is to be further noted that, as used herein, the term "nonwoven fabric" refers to a fabric that has a structure of individual fibers or filaments randomly arranged in a mat-like fashion (including papers). Such fabrics can be made from a variety of processes generally known in the art, including for example airlaid processes, wet-laid processes, hydroentangling processes, staple fiber carding and bonding, and solution spinning.

When present, the binder composition may be applied to the fibrous substrate by a variety of processes generally known in the art. For example, suitable processes for applying the binder composition include, but are not limited to, printing, spraying, electrostatic spraying, coating, flooded nips, metered press rolls, impregnating or by any other technique. The amount of binder composition may be metered and distributed uniformly within the fibrous substrate or may be non-uniformly distributed within the fibrous substrate. Similarly, the binder composition may be distributed throughout the entire fibrous substrate or it may be distributed within a multiplicity of small closely spaced areas. In most embodiments, however, uniform distribution of binder composition is desired.

For ease of application to the fibrous substrate, the binder composition may be dissolved in water, or in a non-aqueous solvent, such as methanol, ethanol, acetone, or the like, with water being the preferred solvent. The amount of binder dissolved in the solvent may vary depending on, for example, the polymer used and the fabric application. Typically, however, the binder solution contains up to about 50 percent by weight of binder composition solids, the binder concentration in the solution being for example in the range of from about 10 to about 30 percent by weight of the binder composition solids, or from about 15 to about 25 percent by weight binder composition solids. Plasticizers, perfumes, coloring agents, antifoams, bactericides, preservative, surface active agents, thickening agents, fillers, opacifiers, tackifiers, detackifiers, and similar additives can also be incorporated into the solution of binder components, if so desired.

Once dry, the coherent fibrous substrate exhibits improved tensile strength, when compared for example to the tensile strength of the untreated wet-laid or dry-laid substrates, and yet has the ability to rapidly fall apart, or disintegrate when placed in soft or hard water (as detailed elsewhere herein) and, and optionally agitated. For example, in various embodiments the dry tensile strength of the fibrous substrate may be increased by at least about 25 percent, as compared to the dry tensile strength of the untreated substrate not containing the binder. Preferably, however, the dry tensile strength of the binder-treated fibrous substrate is increased by at least about 50 percent, 100 percent, 250 percent, 500 percent, or more, as compared to the dry tensile strength of the untreated substrate not containing the binder.

A desirable feature of one embodiment of the present invention (e.g., for an ion-triggerable, water-disintegratable wipe) is that the improvement in tensile strength is effected where the amount of binder composition present, or "add-on", in the resultant fibrous substrate represents only a small portion by weight of the entire treated substrate. The amount of "add-on" can vary for a particular application. However, the optimum amount of "add-on" results in a fibrous substrate which has the desired amount of degree of integrity while in use, and also the desired ability to quickly disperse when placed in a sufficiently diluting amount of water. For example, the binder composition may typically account for about 5 to about 65 percent, by weight, of the total weight of the treated substrate, or from about 7 to about 35 percent, by weight, of the total weight of the treated substrate, or even from about 10 to about 20 percent, by weight, of the total weight of the treated substrate.

The binder-treated, nonwoven fabrics desirably have good in-use tensile strength, as well as, ion triggerability. Additionally, and also desirably, the binder-treated nonwoven fabrics are abrasion resistant and retain significant tensile strength in aqueous solutions containing the specific amount and type of ions disclosed above. Because of this latter property, the binder-treated nonwoven fabrics are well suited for disposable products, such as sanitary napkins, diapers, adult incontinence products, and dry and premoistened wipes (e.g., wet wipes), which can be thrown in a flush toilet after use.

As previously noted, the fibers forming the fabrics above can be made from a variety of materials including natural fibers, synthetic fibers, and combinations thereof, provided the resulting fabric is sufficient hydrophilic (or rendered sufficiently hydrophilic) for use in accordance with the present invention. The choice of fibers depends upon, for example, the intended end use of the finished fabric and fiber cost. For instance, suitable fibrous substrates may include, but are not limited to, natural fibers such as cotton, linen, jute, hemp, wool, wood pulp, etc. Similarly, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc., alone or in combination with one another, may likewise be used. Blends of one or more of the above fibers may also be used, if so desired. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Mercerized, chemically stiffened or crosslinked fibers may also be used.

Synthetic cellulose fiber types include rayon in all its varieties and other fibers derived from viscose or chemically modified cellulose, including regenerated cellulose and solvent-spun cellulose, such as Lyocell. Chemically-treated natural cellulosic fibers can be used, such as mercerized pulps, chemically stiffened or crosslinked fibers, or sulfonated fibers. Recycled fibers, as well as virgin fibers, can be used. Cellulose produced by microbes and other cellulosic derivatives can be used, as well.

As used herein, the term "cellulosic" is meant to include essentially any material having cellulose as a major constituent, and, more specifically, any material comprising at least 50 percent by weight cellulose or a cellulose derivative. Thus, this term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose.

The binder composition may also be applied to other fibers or particles. Other fibers that may be treated with the binder composition include fibers made, for example, from carboxymethyl cellulose, chitin, and chitosan. The binder composition may also be applied to particles, such as sodium polyacrylate super absorbent particles. Super absorbent particles are frequently incorporated onto or into fibrous substrates used for personal care items, especially nonwoven fabrics.

The fiber length may be important in producing the fabrics of the present invention. For example, in some embodiments, such as flushable products, fiber length is of more importance. The minimum length of the fibers depends on the method selected for forming the fibrous substrate. For example, where the fibrous substrate is formed by carding, the length of the fiber should usually be at least about 40 mm (e.g., about 42 mm) in order to ensure uniformity.

Where the fibrous substrate is formed by airlaid or wet-laid processes, the fiber length may in some embodiments desirably be about 0.2 to 6 mm. Although fibers having a length of greater than 50 mm are potentially useable for some applications, it has been determined that when a substantial quantity of fibers having a length greater than about 15 mm is placed in a flushable fabric, though the fibers will disperse and separate in water, their length tends to form "ropes" of fibers, which are undesirable when flushing in home toilets. Therefore, for these products, it is desired that the fiber length be about 15 mm or less (e.g., less than about 12 mm, about 10 mm or even about 8 mm), so that the fibers will not have a tendency to "rope" when they are flushed through a toilet. Although fibers of various lengths are applicable in the present invention, desirably fibers are of a length less than about 15 mm, so that the fibers disperse easily from one another when in contact with water. The fibers, particularly synthetic fibers, can also be crimped, using means known in the art.

The fabrics used in the present invention may be formed from a single layer or multiple layers. In the case of multiple layers, the layers are generally positioned in a juxtaposed or surface-to-surface relationship and all or a portion of the layers may be bound to adjacent layers. Nonwoven webs may also be formed from a plurality of separate nonwoven webs wherein the separate nonwoven webs may be formed from single or multiple layers. In those instances where the nonwoven web includes multiple layers, the entire thickness of the nonwoven web may be subjected to a binder application, or each individual layer may be separately subjected to a binder application and then combined with other layers in a juxtaposed relationship to form the finished nonwoven web.

In one embodiment, the fabric substrates may be incorporated into cleansing and body fluid absorbent products, such as sanitary napkins, diapers, adult incontinence products, surgical dressings, tissues, wet wipes, and the like. These products may include an absorbent core, comprising one or more layers of an absorbent fibrous material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier means to preclude the passage of fluid through the core and on the outer surfaces of the product. Desirably, the barrier means also is water-dispersible. A film of a polymer having substantially the same composition as the aforesaid water-dispersible binder is particularly well-suited for this purpose. In accordance with the present invention, the polymer compositions are useful for forming each of the above-mentioned product components, including the layers of absorbent core, the fluid-pervious element, the wrapping materials, and the fluid-impervious element or barrier means.

E. Wet Wipe Composition

The present invention is directed, in part, to a process for preparing a pre-moistened wipe, or wet wipe, which may optionally include a triggerable binder composition, a fibrous material, and a stratified wetting composition (as detailed elsewhere herein). As noted above, the fibrous material for the wet wipe may be in the form of a woven or nonwoven fabric; however, nonwoven fabrics may be preferred in some embodiments (e.g., a water-dispersible wet wipe), particularly nonwoven fabrics formed from relatively short fibers, such as wood pulp fibers. The minimum length of the fibers depends on the method selected for forming the nonwoven fabric, and/or the desired end use of the fabric. For example, where the nonwoven fabric is formed by a wet or dry method, the fiber length is preferably in the range of from about 0.1 mm to 15 mm, or from about 0.5 mm to about 12 mm, or from about 1 mm to about 10 mm.

In various embodiments, particularly for an ion-triggerable, water-disintegratable wipe, the nonwoven fabric preferably has a relatively low wet cohesive strength when it is not bonded together by an adhesive or binder material. When such nonwoven fabrics are bonded together by a binder composition, which as noted above loses its bonding strength in for example tap water or sewer water, the fabric will break up readily by the agitation provided by flushing and moving through the sewer pipes.

The finished wipes may be individually packaged, desirably in a folded condition, in a moisture proof envelope or packaged in containers holding any desired number of sheets in a water-tight package with a wetting composition applied to the wipe. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (San Jose, Calif.); Shimizu Manufacturing (Japan), and the devices disclosed in U.S. Pat. No. 4,667,890. Solid-wound coreless rolls may offer more product for a given volume and can be adapted for a wide variety of dispensers.

The wetting composition may applied to the fibrous substrate using means known in the art in order, for example, to ensure that it is initially distributed uniformly through substantially the entire wet wipe base sheet or substrate. However, it is to be noted that it may be applied to the base sheet or substrate in any way generally known in the art (including, for example, application of the wetting composition to only one side of the substrate). Once applied and destabilized in some way (either before or after application to the fibrous substrate), phase separation, and thus stratification, of the phases of the wetting composition will occur over a given period of time (as detailed elsewhere herein.)

The concentration or "add-on" level of the wetting composition in the wet wipe product (either before or after phase separation has occurred) may be optimized for a given application, and/or the composition of the base sheet to which the wetting composition is applied. Typically, however, relative to the weight of the dry fabric or base sheet, the wipe may contain from about 100 percent to about 400 percent of the wetting composition, or from about 125 percent to about 350 percent of the wetting composition, or from about 150 percent to about 300 percent of the wetting composition, or from about 175 percent to about 275 percent of the wetting composition, or from about 200 percent to about 250 percent of the wetting composition. In one particular embodiment, the concentration of the wetting composition in the resulting wet wipe is about 235 percent, based on the dry base sheet weight.

In this regard it is to be noted that the concentration of the wetting composition may alternatively be expressed in terms of unit weight of the emulsion per unit weight of the dry base sheet. For example, the concentration or "add-on" level of the wetting composition may typically be in the range of from about 1 gram per gram of dry base sheet to about 4 grams, or about 1.25 to about 3.5 grams, or about 1.5 to about 3 grams, or about 1.75 to about 2.75 grams, or about 2 to about 2.5 grams, the concentration in one particular embodiment being 2.35 grams per gram of dry base sheet.

As previously noted, the wetting composition is designed or caused to phase separate, and thus stratify, within the fibrous substrate within a given period of time, after for example being treated or acted upon in some way. For example, as further detailed elsewhere herein, a stable emulsified wetting composition may be applied to the wipe and designed to remain stable until acted upon in some way to cause phase separation to occur (e.g., by heating or freezing the wipe). Alternatively, the emulsified wetting composition may be treated or acted upon in some way to destabilize the emulsion prior to it being applied to the fibrous substrate, phase separation thus occurring relatively soon after being applied to the fibrous substrate. For example, in one alternative embodiment, a concentrated and stable emulsified wetting composition may be diluted with a quantity of a salt solution, the salt concentration being sufficient to destabilize the emulsion over a desired period of time (and optionally sufficient to render the fibrous base sheet insoluble in the wetting composition, in the case of an ion-triggerable, water-disintegratable wipe). Alternatively, however, the wetting composition may be stable in the presence of the salt concentration therein (or the added thereto, as part of a dilution step).

Desirably, the pre-moistened or wet wipes of the present invention may be wetted with a composition that, in addition to exhibiting phase separation or stratification at the desired time, additionally has one or more of the following properties: (1) it is compatible with, when present, a triggerable binder composition, particularly the above-described binder composition; (2) it enables the pre-moistened wipe to maintain its wet strength during preparation, storage and usage (including dispensing), as well as dispersibility when disposed of (e.g., placed in a toilet bowl and flushed); (3) it does not cause skin irritation; (4) it reduces tackiness of the wipe, and provides tactile properties, such as skin glide and a "lotion-like feel"; and, (5) it acts as a vehicle to deliver "moist cleansing" and other skin health benefits.

F. Wet Wipe Strength and Thickness

Desirably, in one or more embodiments, the wet wipes of the present invention possess an in-use wet tensile strength of at least about 100 g/in (e.g., about 125 g/in, about 150 g/in, or more) when soaked in the wetting composition (e.g., a concentration of about 100% to about 400%, or about 125% to about 375%, etc., by weight, of the wetting composition relative to the dry weight of the base sheet) that optionally contains, for example, more than about 0.5% by weight of a monovalent and/or a divalent salt, such as for example, NaCl, $ZnCl_2$ and/or $CaCl_2$, or mixtures thereof. Additionally, in the case of an ion-triggerable, water-disintegratable wet wipe, the wipe preferably has a tensile strength of less than about 30 g/in (e.g., about 25 g/in, about 20 g/in, or less), after being soaked in soft water or hard water (e.g., containing up to about 500 ppm concentration of $Ca^{2+}$ and/or $Mg^{2+}$) for about 24 hours or less (e.g., less than about 20 hours, about 15 hours, about 10 hours, about 5 hours, or even about 1 hour). More desirably, in one particular embodiment, an ion-triggerable, water-disintegratable wet wipe of the present invention possesses an in-use tensile strength of at least about 200 or even about 300 g/in when soaked in the wetting composition, and a tensile strength of less than about 75 g/in or even 50 g/in after being soaked in soft or hard water for the noted period of time. Even more desirably, in such an embodiment, the water-disintegratable wet wipe of the present invention possesses an in-use tensile strength of greater than about 300 g/in (e.g., about 325 g/in, about 350 g/in or more) when soaked in such the wetting composition, and a tensile strength of less than about 30 g/in (e.g., about 25 g/in, about 20 g/in, or less) after being soaked in soft or hard water for the noted period of time.

It is to be noted that products with higher basis weights than water-disintegratable (e.g., flushable) wet wipes may have relatively higher wet tensile strength. For example, products such as pre-moistened towels or hard-surface cleaning wipes may have basis weights above about 70 gsm, such as for example from about 80 gsm to about 150 gsm. Such products can have CDWT (cross deckle wet tensile strength) values of about 500 g/in or greater, and after soaking values of about 150 g/in or less (e.g., about 100 g/in or less, or about 50 g/in or less).

It is to be further noted that the wet wipes of the present invention may have essentially any thickness generally known in the art, which is suitable for the intended use of the wipe. For example, these wipes may have an average thickness within the range of about 0.1 mm to about 5 mm, or from about 0.2 mm to about 1 mm, or from about 0.3 mm to about 0.8 mm. Thickness can be controlled, for example, by the application of compaction rolls during or after web formation, by pressing after the binder composition and/or the wetting composition has been applied, or by controlling the tension of winding when forming a roll good.

G. Methods for Wipe Preparation

As previously noted above, the present invention is further directed to various processes for preparing a wet wipe product comprising a stratified wetting composition, as further detailed herein below. However, generally speaking, in one particular embodiment, the process may involve the application of a dilute oil-in-water emulsified wetting composition to the fibrous substrate of the wipe and then acting upon the wipe in some way to destabilize the wetting composition therein (such that phase separation occurring within less than about 1 week and more than about 10 minutes). Destabilization may be achieved, for example, by heating or chilling (e.g., freezing) the wet wipe. In one particular embodiment, the process may additionally involve the initial formation of the dilute oil-in-water emulsified wetting composition by diluting a concentrated form of the emulsified wetting composition.

In an alternative embodiment, the dilute oil-in-water emulsified wetting composition may be destabilized prior to the application thereof to the fibrous substrate. Destabilization may be achieved by heating or chilling the composition, by adjusting the pH thereof (e.g., the addition of an acid or a base thereto), or by adding salt thereto. In one particular embodiment, the process may additionally involve the initial formation of the dilute oil-in-water emulsified wetting composition by diluting a concentrated form of the emulsified wetting composition. In fact, in one such process the dilution step and the destabilization step may be the same (e.g., a concentrated form of the emulsified wetting composition may be diluted with a salt solution, and acid solution, or a basic solution, in order to form a dilute, destabilized oil-in-water emulsified wetting composition).

In yet another alternative embodiment, the wipe may be prepared by contacting the fibrous substrate with a concentrated form of the oil-in-water emulsified wetting composition. An aqueous solution is also applied to the fibrous substrate, either before or after application of the concentrated form of the oil-in-water emulsified wetting composition, in order to form a dilute, oil-in-water emulsified wetting composition in situ therein. The dilute, oil-in-water emulsified wetting composition may then be destabilized in some way (e.g., by heating or chilling the wipe). Alternatively, a dilute, destabilized oil-in-water emulsified wetting composition may be formed in situ within the wipe, wherein the act of dilution (by contacting the concentrated form of the oil-in-water emulsified wetting composition with the aqueous solution) also results in destabilization.

In yet another alternative embodiment, the wipe may be prepared by contacting the fibrous substrate with an organic (or oil) based liquid and an aqueous (or water) based liquid, which are not in the form of an emulsion and do not form a stable emulsion. After a period of time, these liquids migrate to the surface (or surface regions) and the bulk region, respectively, to form a wet wipe having a stratified wetting composition therein.

In yet another alternative embodiment, the wipe may be prepared by destabilizing the oil-in-water emulsion, either before or after it has been applied to the fibrous substrate, using some other means known to one of ordinary skill in the art for breaking an emulsion (see, e.g., means disclosed in McGraw Hill Concise Encyclopedia of Science and Technology, which references, for example, (i) applying a high potential alternating current or electric field to the wipe or emulsion, (ii) treating the wipe or emulsion with ultrasonic energy or waves of low intensity, and/or (iii) adding multivalent ions to the wipe or emulsion having a charge opposite to that of the emulsion droplets).

It is to be noted that, regardless of the method utilized to form the wet wipe of the present invention, preferably phase separation occurs with the fibrous substrate within the time period detailed elsewhere herein above. It is to be further noted, and also as detailed elsewhere herein above, that in one or more of the above embodiments the dilute, oil-in-water emulsified wetting composition may have a salt concentration of at least about 0.5 weight percent, based on the total weight of the emulsified wetting composition, prior to said destabilizing treatment, or alternatively, after (even as a result of) said destabilizing treatment. Additionally, in this or another embodiment, said process may comprise contacting the fibrous substrate with a triggerable binder formulation prior to said wetting composition, wherein said triggerable binder formulation is insoluble in the emulsified wetting composition and dispersible in water.

It should be noted that all emulsions, as known to those skilled in the art, are inherently thermodynamically unstable (e.g., the free energy of formation is positive), and given enough time, all emulsions will eventually separate. However, an emulsion that does not show separation over a lengthy period of time can be referred to as "kinetically stable" because the rate of separation is extremely slow. The various approaches to "destabilizing" an emulsion described herein accelerate this process. The relatively short period of time before separation is visible is typically referred to as the "period of kinetic stability."

The above-noted embodiments are further detailed and illustrated herein below.

1. Using an Anionic Emulsifier

One method of preparing wipe of the present invention is to add a destabilizing compound to a stable oil-in-water emulsion, and apply the resulting formulation to the wipe within the shortened period of kinetic stability (that is, before phase separation begins). For ease of handling, the destabilizing compound may be dissolved in a small amount of water, although this is not necessary.

In one exemplary embodiment, an emulsion made with an anionic emulsifier, such as sodium stearate or triethanolamine stearate at an inclusion level of between about 3 and about 5 weight percent (based on the total weight of the oil-in-water emulsion), can be destabilized by adding a low amount of electrolyte, such as for example between about 0.25 to about 10 weight percent, or between about 0.5 and about 8 weight percent (based on the total weight of the oil-in-water emulsion), of an inorganic salt, optimally sodium chloride. Alternatively, an emulsion made with an anionic emulsifier, such as sodium stearate or triethanolamine stearate, can be destabilized by reducing the pH (e.g., reducing the pH of an emulsion having an inclusion level of between about 0.5 and about 6 weight percent of the anionic emulsifier). This can be done by the addition of a sufficient quantity of acid to reduce the pH to, for example, a pH of about 5 or lower.

In this regard it is to be noted that, depending upon the pH of the starting emulsion, the amount of acid required to reduce the pH to the desired level may vary, but this can be readily calculated by one of ordinary skill in the art. Strong acids, such as hydrogen chloride, sulfuric acid, nitric acid, or other known strong acids, can be used. In this regard it is to be further noted that because strong acids are typically available as aqueous solutions, a negligibly small amount of water will also be added to the emulsion. It is also possible to use a weak acid, such as malic acid, citric acid, or any of the wide variety of known weak acids, also at an inclusion level calculated using the starting emulsion pH and the known dissociation constant of the weak acid, according to methods known by those of ordinary skill in the art. A listing of acid dissociation constants may be found in the CRC Handbook of Chemistry and Physics.

2. Using a Cationic Emulsifier

By way of a second example of a means to destabilize an emulsion by adding a destabilizing compound, an emulsion made with a cationic emulsifier, such as behentrimonium chloride at an inclusion level of between about 0.5 and about 6 weight percent (based on the total weight of the oil-in-water emulsion), can be destabilized by addition of a moderate amount of electrolyte, such as between about 0.25 and about 10 weight percent, or between about 0.5 and about 8 weight percent (based on the total weight of the oil-in-water emulsion), of an inorganic salt, such as in one preferred embodiment sodium chloride. Emulsions made with cationic emulsifiers can also be destabilized by shifting the pH to a higher level, such as for example above about 8. A higher pH can be obtained by the addition of a strong base, such as for example sodium hydroxide, potassium hydroxide, or the like. A weak base may also be used or added, in order to adjust the pH. Consistent with the comments provided above, it is to be noted that the amount of an acid (e.g., strong acid) or base (e.g., weak base) may be readily calculated by one of ordinary skill in the art.

3. Using a Polymeric Emulsifier

A third example of a method of adding a destabilizing compound to a stable emulsion involves the use of a polymeric emulsifier, such as for example one of the emulsifiers available under the tradenames PEMULEN™ from Noveon or SEPIGEL™ from Seppic. A stable emulsion containing, for example, between about 0.05 and about 0.5% of a PEMULEN™ polymeric emulsifier, or alternatively between about 1 and about 5% of a SEPIGEL™ polymeric emulsifier, can be destabilized by addition of a low amount of electrolyte, such as between about 0.1 and about 10 weight percent, or between about 0.25 and about 6 weight percent (based on the total weight of the oil-in-water emulsion), of an inorganic salt, such as in one preferred embodiment sodium chloride. Certain polymeric emulsifiers, such as those available under the name PEMULEN™, can also be destabilized by the addition of an acid sufficient to reduce the pH below about 4. This can be done by the addition of a strong or weak acid at a sufficient inclusion level, as described above (i.e., consistent with the comments provided above, it is to be noted that the amount of an acid, such as a strong acid, or base, such as a weak base, may be readily calculated by one of ordinary skill in the art). Certain polymeric emulsifiers, such as those available under the name PEMULEN™, can also be destabilized by addition of base sufficient to increase the pH above about 9.

4. Preparation Using a Concentrated Emulsion

It is to be noted that, as an alternative to one or more of the above-noted methods, which may be preferred in some instances, an aqueous solution of a destabilizing compound may be added to or mixed with a concentrated, stable emulsion, the resulting solution or diluted emulsion then being applied to the wipe within the shortened period of kinetic stability (that is, before phase separation begins). All the approaches described in the preceding paragraphs are applicable.

In this optional approach or embodiment, a low to moderate amount of salt can be used to destabilize an emulsion made with, for example, an appropriate anionic, cationic, or polymeric emulsifier. Strong or weak acids, such that the final, diluted emulsion has a pH of less than about 5 or even lower, can be used to destabilize emulsions made with, for example, an appropriate anionic emulsifier, cationic emulsifier, or polymeric emulsifier (such as those available under the name PEMULEN™). Finally, strong or weak bases, such that the final, diluted emulsion has a pH of about 8 or higher, can be used to destabilize emulsions made with, for example, an appropriate cationic emulsifier.

An example of this second, and in some instances preferred, embodiment or approach of creating a wipe of the invention is as follows (and as further illustrated in Example 2, presented herein below). A concentrated emulsion formulation can be made using the polymeric emulsifier PEMULEN™ TR-1 (commercially available from Noveon). This concentrated emulsion can be diluted with an equal amount of a solution (e.g., about 4% by weight) of sodium chloride. The final diluted formulation contains about half the concentration of emulsion components (by weight) and about 2% (by weight) sodium chloride. As previously noted, the diluted formulation can be applied to a wipe in the short period of kinetic stability. After application, the emulsion will separate over a period of time, and the lubricious oil phase tending to migrate towards the outer surface of the wipe, and the aqueous phase tending to remain within the interior portion or region of the hydrophilic wipe substrate.

In this regard it is to be noted that, in yet another alternative approach to preparing the wet wipe of the present invention, the serial application of two formulations to the wipe may be employed. For example, a concentrated emulsion (as detailed elsewhere herein above), can be applied to a wipe before the addition of an aqueous solution containing an appropriate destabilizing compound in sufficient quantity such that the concentrated emulsion is diluted (and destabilized) to the desired level. Alternatively, the first step may consist of applying an aqueous solution containing an appropriate destabilizing compound, and a concentrated emulsion may be added to the wipe in a distinct second step. In either case, the composition and/or amount of the concentrated emulsion and/or the aqueous solution are such that the resulting mixture phase separates within the shortened window of kinetic stability, creating the stratified wipe of the present invention.

5. Destabilization by Heating or Cooling

An additional approach to creating the wipe of the present invention does not require the addition of a destabilizing compound. For example in one alternative approach, a stable emulsion (e.g., an emulsion that is stable at room temperature) is applied to the fibrous substrate of the wipe, and then the resulting wipe is then heated to a temperature above room temperature (e.g. a temperature of about 50° C., about 60° C., or even about 70° C.), and for a period of time (e.g., about 1 hour, about 12 hours, about 24 hours, or even about 3 days, about 5 days or even about 1 week), the time/temperature combination being sufficient to destabilize the emulsion within the wipe.

In this regard it is to be noted that it is known to those of ordinary skill in the art that formulations containing a relatively low amount of an emulsifier may be stable at room temperature but may separate at elevated temperatures. Appropriate levels of emulsifiers may be, for example, between about 0.1 and about 10 weight percent, or between about 0.5 and about 8 weight percent, or between about 1 and about 6 weight percent. Emulsifiers may be selected from, for example, cationic, anionic, nonionic, zwitterionic, amphoteric emulsifiers, or even polymeric emulsifiers. For polymeric emulsifiers, however, the appropriate level may be even lower (e.g., between about 0.05 and about 2).

In yet another alternative approach, a stable emulsion (e.g., an emulsion that is stable at room temperature) is applied to the fibrous substrate of the wipe, and then the resulting wipe is then cooled to a temperature below room temperature, and more specifically is subjected to one or more freeze-thaw cycles. A freeze thaw cycle is generally defined as subjecting the wipe for a period of time of about 24 hours to a temperature of less than about 0° C. (e.g., about −5° C., about −10° C., or less), followed by a period of about 24 hours acclimation time to return the wipe to room temperature.

In this regard it is to be noted that it is known to those of ordinary skill in the art that formulations containing a relatively low amount of an emulsifier may be stable at room temperature but may separate under the added stress of one or more freeze-thaw cycles. Emulsifiers may be selected from, for example, cationic, anionic, nonionic, zwitterionic, amphoteric emulsifiers, or even polymeric emulsifiers. For polymeric emulsifiers, however, the appropriate level may be even lower (e.g., between about 0.05 and about 2).

6. Preparation Using Separate Oil and Aqueous Phases or Components of the Wetting Composition It is to be noted that yet another possible alternative to creating a wipe of the present invention involves the use of immiscible oil and aqueous phases or components of the wetting composition. In such an approach, these components may be mechanically mixed, using means generally known in the art, and rapidly applied to the wipe. The oil phase may contain a low level of emulsifier, which is insufficient to create a stable emulsion (where "stable" is as defined elsewhere herein), or it may contain no emulsifier at all. The formulation will separate after the short period of kinetic stability is expired.

7. Other Approaches

It is to be noted that other approaches are possible to for creating the stratified wipe of the present invention. For instance, it is known to those of ordinary skill in the art that emulsions may be destabilized through application of high potential alternating electric fields, through low intensity ultrasonic waves, or through vibration. The finished emulsion-moistened wipes may be exposed to one or more of these treatments, using means generally known in the art, to destabilize the emulsion and create a stratified wipe of the present invention.

8. Preparation Steps Using an Emulsified Wetting Composition

The wet wipes of the present invention can be made using various methods generally known in the art for wet wipe preparation, and/or as detailed elsewhere here. For example, in one approach for preparing an ion-triggerable, water-disintegratable wet wipe, a binder composition may be applied to a fibrous substrate as part of an aqueous solution or suspension, wherein subsequent drying is needed to remove the water and promote binding of the fibers, thus forming the base sheet of the wipe (i.e., the sheet prior to application of the emulsified wetting composition). In this approach, during drying the binder migrates to the crossover points of the fibers and becomes activated as a binder in those regions, thus providing acceptable strength to the substrate.

For purposes of illustration, the following method steps may be used in wet wipe preparation: (1) preparing or providing an absorbent fibrous substrate, which may optionally not be highly bonded (e.g., an unbonded airlaid fibrous material, a tissue web, a carded web, fluff pulp, etc.); (2) optionally applying a binder composition (e.g., a triggerable binder composition, or more particular a cationic polymer binder composition) to the substrate, typically in the form of a liquid, suspension, or foam, and then drying the binder-treated substrate to promote bonding of the substrate; (3) applying a wetting composition (e.g., a stable, emulsified wetting composition, or another wetting composition, prepared for example as detailed herein above) to the fibrous substrate (or optionally the binder-treated fibrous substrate); (4) optionally treating the wetted substrate to destabilize the emulsified wetting composition (as detailed herein above), thus causing phase separation of the emulsion to occur; and, (5) packing the wetted substrate (e.g., placing the wetted substrate in roll form or in a stack and packaging the product).

In this regard it is to be noted that packaging may occur either before or after said treatment to destabilize the emulsion has occurred. For example, in one approach, the wetted substrate may be treated in order to destabilize the emulsion, such that phase separation occurs some period of time after packaging has occurred. Alternatively, the destabilizing treatment may be performed after packaging has occurred, the treatment being performed for example on the wetted substrate while in the package, or alternatively being performed after removing the wetted substrate from the package.

In this regard it is to be further noted that, in one particularly preferred embodiment, the conditions and/or timing of the treatment to destabilize the emulsified wetting composition is such that phase separation does not begin prior to application of the wetting composition to the fibrous substrate. Without being held to any particular theory, it is generally believed that is it easier and/or more efficient to apply the wetting composition to the fibrous substrate while still being a homogenous emulsion.

It is to be further noted that this destabilizing treatment may be achieved using any means generally known in the art, and/or as detailed herein above, for destabilizing oil-in-water emulsions, such that phase separation occurs within the desired period of time.

It is to be still further noted that alternative approaches to the above-noted methods of preparing the wet wipe may be employed without departing from the scope of the present invention. For example, in one alternative approach in which a binder is used, the dry binder-treated substrate may be placed in roll form or in a stack and packaged after the completion of steps 1-3 above, followed thereafter by the addition of the wetting composition. The wetted substrates could then either be used immediately, or repackaged for future use.

It is to be still further noted that application of the binder composition, and/or the emulsified wetting composition, to the substrate (or binder-treated substrate) can be by essentially any means known in the art, including for example: spraying; foam application; immersion in a bath; curtain coating; coating and metering with a wire-wound rod; passing of the substrate (or binder-treated substrate) through a flooded nip; contacting with a pre-metered wetted roll coated with the binder composition, or emulsified wetting composition; pressing the substrate, or binder-treated substrate, against a deformable carrier containing the binder composition (or wetting composition), such as a sponge or felt, to effect transfer into the substrate; printing, such as gravure, inkjet, or flexographic printing; and any other means known in the art.

As noted elsewhere herein, the emulsified wetting composition may generally be prepared using means known in the art. For example, the emulsion may be prepared by: (1) forming what will be the aqueous phase of the emulsion by mixing a quantify of one or more of the desired components thereof with a quantity of water (e.g., mixing a salt, when for example an ion-triggerable, water-disintegratable wipe is being prepared), with agitation and/or heating as needed, followed by the optional addition of other desired water-soluble components or additives; (2) forming what will be the organic phase of the emulsion by mixing the various components of the organic phase (e.g., emulsifier, emollients, etc.), with agitation and/or heating as needed; (3) contacting the aqueous phase and the organic phase, with agitation and/or heating as needed; and, optionally, (4) the addition of any other desired components or additives for the wetting composition.

9. Concentrated, Emulsified Wetting Composition

It is to be additionally noted that the use of a concentrated wetting composition is advantageous for a number of reasons, including decreased shipping and storage costs resulting from the reduced total volume of the emulsion. Generally speaking, the composition of the concentrated, emulsified wetting composition differs from the dilute, or ready-to-use, form of the emulsified wetting composition in that it contains less water and/or salt in the aqueous phase of the emulsion. For example, in various embodiments, the amount or concentration of water and/or salt in the concentrated, emulsified wetting composition may be reduced, as compared to the amount or concentration of water and/or salt in the diluted composition, by at least about 25 weight percent, about 50 weight percent, about 75 weight percent, about 85 weight percent or more. In one particular embodiment, the concentrated, emulsified wetting composition contains essentially no salt (i.e., the concentrated, emulsified wetting composition is substantially free of the insolublizing agent or salt), while the amount or concentration of water therein is reduced, relative to the amount or concentration of water in the dilute, emulsified wetting composition, by at least about 50 weight percent, about 75 weight percent, about 85 weight percent or more. In an alternative embodiment, however, the concentrated, emulsified wetting composition contains essentially all of, or at least some portion of, the salt present in the final, diluted emulsion (i.e., the concentrated, emulsified wetting composition contains at least about 25 weight percent, at least about 50 weight percent, at least about 75 weight percent, or even at least about 95 weight percent, of the insolublizing agent or salt present in the final, diluted emulsion), while the amount or concentration of water therein is reduced, relative to the amount or concentration of water in the dilute, emulsified wetting composition, by at least about 50 weight percent, about 75 weight percent, about 85 weight percent or more.

In this regard it is to be noted that, as used herein, "substantially free" of the insolublizing agent or salt (as well as variations thereof) generally refers to a concentrated, emulsified wetting composition that has essentially no detectable concentration of the insolublizing agent or salt, using means of detection or analysis known in the art, or has a concentration thereof that is less than about 0.1 weight percent, about 0.05 weight percent, or even 0.01 weight percent of the insolublizing agent or salt, based on the total weight of the concentrated, emulsified wetting composition.

In view of the foregoing, it is to be noted that the weight ratio of the aqueous phase to the oil phase in the concentrated, emulsified wetting composition is typically greater than about 1:1 and less than about 10:1, or greater than about 1.2:1 and less than about 8:1, or greater than about 1.4:1 and less than about 6:1, or greater than about 1.5:1 and less than about 4:1. For example, in various embodiments the weight ratio of the aqueous phase to oil phase in the concentrated, emulsified wetting composition is about 1.5:1, about 2:1, about 3:1 or about 4:1.

The more concentrated form of the emulsified wetting composition, as expected, typically has a higher viscosity, as compared to the diluted composition, at low shear. For example, prior to dilution, the concentrated, emulsified wetting composition may even have a cream-like consistence or appearance, the viscosity for example being as high as about 600,000 cps. Typically, however, at a shear of 0.5 rpm, the viscosity of the concentrated, emulsified wetting composition may be greater than about 25,000 cps, about 35,000 cps, about 45,000 cps, about 55,000 cps, about 65,000 cps, about 75,000 cps or more (e.g., about 100,000 cps, about 150,000 cps, about 200,000 cps, about 250,000 cps, about 500,000 cps or more).

As noted elsewhere herein, the emulsified wetting composition, either in dilute or concentrated form, may generally be prepared using means known in the art. For example, the concentrated emulsion may be prepared by: (1) forming what will be the organic phase of the emulsion by mixing the various components of the organic phase (e.g., emulsifier, emollients, etc.), with agitation and/or heating as needed (e.g., mixing and heating to about 50° C., about 75° C. or more); (2) contacting the organic phase with a quantity of water sufficient to form an oil-in-water emulsion, with agitation and/or heating as needed; and, optionally, (3) the addition of any other desired components or additives for the wetting composition. Once prepared, the concentrated emulsion may be packaged and stored for future use, or alternatively it may be used as soon as possible after preparation.

When used to prepare the wet wipe of the present invention, including for example an ion-triggerable, water-disintegratable wet wipe, wet wipe preparation additionally involves the step of diluting the concentrated, emulsified wetting composition by adding a sufficient quantity of water and/or the salt (e.g., adding a quantity of water which contains a quantity of salt sufficient to, as further detailed herein, achieve the desired effect on the wipe base sheet and, when present, the triggerable binder composition). Additionally, other desirable components of the wetting composition (e.g., pH adjusting additives, fragrances, emollients, etc.) may also be added to the concentrated, emulsified wetting composition prior to use.

In this regard it is to be noted that, in one particular embodiment, the concentrated emulsion is formed using an emulsifier that is unstable to a given salt and/or threshold salt concentration. More specifically, in one embodiment of the present invention, a wet wipe comprising a stratified wetting composition is formed by diluting a concentrated, emulsified wetting composition with a salt solution, wherein as a result of this dilution a destabilized emulsified wetting composition is form. This dilute, but destabilized, emulsified wetting composition is then applied to the fibrous substrate, preferably before phase separation begins. Among the exemplary concentrated, emulsified wetting compositions are those comprising an anionic and/or polymeric emulsifier, which are known to form emulsions that may be destabilized in the presence of a salt, or in the presence of a concentration of salt above some threshold concentration.

It is to be further noted that, in an alternative embodiment, the concentrated emulsified wetting composition may be diluted with a salt-containing solution wherein the resulting diluted emulsified wetting composition is destabilized not by the addition of the salt, but rather by the addition of some other component or additive, such as an acid or base (or more generally a pH modifying agent). In this particular embodiment, a sufficient quantity of acid or base is added to lower or raise, respectively, the pH to a level which acts to destabilize the emulsified wetting composition.

It is to be still further noted that the process steps for preparing the wet wipe of the present invention, and/or the order of those steps, may be other than herein described without departing from the scope of the present invention. For example, in one alternative embodiment, rather than diluting the concentrated emulsion with an aqueous solution comprising water and a destabilizing agent of some kind (e.g., a salt or a pH modifying agent), this aqueous solution may be applied directly to the fibrous substrate, followed by application of the concentrated emulsion directly to the fibrous substrate (or vice versa). In this embodiment, the aqueous solution and the concentrated emulsion will naturally mix (due, for example, to the absorbent or wicking properties of the fibrous substrate), resulting in the dilution and destabilization of the concentrated emulsion, followed ultimately by phase separation and stratification of the wetting composition.

It is to be still further noted that, although in a preferred embodiment the concentrated, emulsified wetting composition is used to prepare an ion-triggerable, water-disintegratable wet wipe, it may alternatively be used to prepare a wipe that is not water-disintegratable, without departing from the intended scope of the present invention.

Having described the invention in detail, it will be apparent that modifications and variations are possible without departing from the scope of the invention defined in the appended claims.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

In this Example, a formulation was made with silicone phospholipids, and more specifically has the following composition:

| | |
|---|---|
| Water = | 89.7 wt %; |
| Monasil PCA (PCA dimethicone) = | 5 wt %; |
| Cetiol HE (PEG-7 glyceryl cocoate) = | 1.5 wt %; |
| Propylene Glycol = | 1.5 wt %; |
| Glydant Plus = | 0.3 wt %; |
| Sodium Chloride = | 2 wt %. |

This formulation is known to be unstable, and thus phase separate, over time. Water-disintegratable or dispersible wipes were made with this formulation and allowed to age at room temperature for 1 week. At the end of the 1 week period, another batch of the same formulation was made, and another set of wipes was prepared therefrom. Both set of these wipes were then immediately evaluated in a blind test by 10 panelists. All but one panelist detected a difference between the feel of these wipes. The aged wipes were generally described as "silkier," or "softer," or "less sticky," and sometimes perceived as thicker than the freshly prepared wipes. These results suggest that phase separation within the aged wipes was responsible for the improved hand feel.

EXAMPLE 2

A stratified wipe may be prepared by preparing a concentrated wipe emulsion according to formulation in the following table. The batching procedure would be as follows:
1) Phase 1: Add ingredients with mixing and while heating to 40° C. until homogeneous.
2) Disperse PEMULEN™ in PHA while heating to 40° C. Add to Phase 1 with high agitation and allow to hydrate 30 minutes.
3) Combine the rest of the organic phase and heat to 40° C. Add to water phase with mixing for 10 minutes.
4) Neutralize with KOH 10% to an approximate pH of between 6.5 and 7. Begin cooling to room temperature.
5) Add preservative and mix until room temperature is reached.

| Stratified Wipe Concentrate | | |
|---|---|---|
| Trade Name | INCI Name | % wt |
| Phase 1 | | |
| Water | Water | 91.65 |
| Butylene Glycol | Butylene Glycol | 1.25 |
| Versene Na2 (Dow) | Disodium EDTA | 0.05 |

| -continued | | |
|---|---|---|
| Stratified Wipe Concentrate | | |
| Trade Name | INCI Name | % wt |
| Phase 2 | | |
| Hetester PHA (Bernel/Alzo) | Propylene Glycol Isoceteth-3 Acetate | 2.50 |
| PEMULEN ™ TR-1 (Noveon) | Acrylates/C10-30 Alkyl Acrylate Crosspolymer | 0.20 |
| Phase 3 | | |
| Safflower Oil | Carthamus Tinctorius (Safflower) Seed Oil | 1.50 |
| Caprylic/Capric Triglyceride | Caprylic/Capric Triglyceride | 1.00 |
| DC 200 100 cst (Dow Corning) | Dimethicone | 0.50 |
| Ceraphyl SLK (ISP) | Isodecyl Neopentanoate | 0.50 |
| Vitamin E Acetate | Tocopheryl Acetate | 0.05 |
| Phase 3 | | |
| KOH 10% | Potassium Hydroxide | q.s. |
| Phase 4 | | |
| Paragon MEPB (McIntyre) | Phenoxyethanol, Methylparaben, Ethylparaben, Propylparaben, Butylparaben, Isobutylparaben | 0.80 |
| Total | | 100.00 |

This formulation will have a viscosity in the range of between 5,000 and 10,000 centipoise. It may be stored until ready to use. To prepare the wipes of the invention, the wipe concentrate is mixed with an equal amount (by weight) of a 4% sodium chloride solution. The newly diluted, and destabilized, emulsion is applied to the wipe. The emulsion is expected to stratify on the wipe within about 24 hours.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions or products, and/or methods for the preparation thereof, without departing from the scope of the invention, it is intended that all matter contained in the above description shall be interpreted as illustrative and not in a limiting sense.

What is claimed is:

1. A wet wipe having a stratified wetting composition therein, the wipe comprising:
    a fibrous substrate having a front surface region and a back surface region generally parallel thereto, and a bulk region between said front surface region and back surface region; and,
    a wetting composition in contact with the fibrous substrate, the wetting composition comprising an oil phase and an aqueous phase, wherein a concentration of one or more oil phase components is greater in the front and/or back surface regions of the substrate than a concentration of the same component, or components, in the bulk region of the substrate, and further wherein a concentration of one or more aqueous phase components is greater in the bulk region of the substrate than a concentration of the same component, or components, in the front and back surface regions of the substrate.

2. The wet wipe of claim 1, wherein the concentration of one or more components of the oil phase in the front and back surface regions is at least about 15 percent greater than the average concentration of the component or components, based on the total weight of the component in the wetting composition.

3. The wet wipe of claim 1, wherein said wipe further comprises a binder formulation that is insoluble in the wetting composition and dispersible in water, said wipe being an ion-triggerable, water-dispersible wipe.

4. The wet wipe of claim 3, wherein the wetting composition comprises an emulsifier selected from the group consisting of a nonionic emulsifier, an anionic emulsifier, a cationic emulsifier, an amphoteric emulsifier, a zwitterionic emulsifier, a polymeric emulsifier, or a combination of two or more thereof.

5. The wet wipe of claim 4, wherein the concentration of the emulsifier in the wetting composition is greater than about 0.05 weight percent and less than about 10 weight percent, based on the total weight of the wetting composition.

6. The wet wipe of claim 3, wherein binder formulation comprises an ion triggerable cationic polymer having the structure:

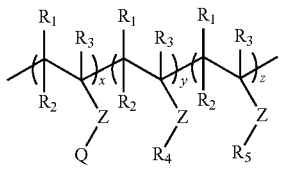

wherein: x is equal to about 1 to about 15 mole percent; y is equal to about 60 to about 99 mole percent; z is equal to 0 to about 30 mole percent; Q is selected from $C_1$ to $C_4$ alkyl ammonium, quaternary $C_1$ to $C_4$ alkyl ammonium and benzyl ammonium; Z is selected from —O—, —COO—, —OOC—, —CONH—, and —NHCO—; $R_1$, $R_2$, $R_3$ are each independently selected from hydrogen and methyl; $R_4$ is selected from methyl and ethyl; and $R_5$ is selected from hydrogen, methyl, ethyl, butyl, ethylhexyl, decyl, dodecyl, hydroxyethyl, hydroxypropyl, polyoxyethylene, and polyoxypropylene.

7. A process for preparing a wet wipe comprising a stratified wetting composition therein, the process comprising:
applying an oil-in-water emulsified wetting composition to a fibrous substrate of the wipe, the fibrous substrate having a front surface region and a back surface region generally parallel thereto, and a bulk region between said front surface region and back surface region; and,
treating the wetted fibrous substrate to destabilize the wetting composition and cause phase separation of the wetting composition to occur within the fibrous substrate,
wherein after said phase separation, a concentration of one or more oil phase components is greater in the front and back surface regions of the substrate than a concentration of the same component, or components, in the bulk region of the substrate, and further wherein a concentration of one or more aqueous phase components is greater in the bulk region of the substrate than a concentration of the same component, or components, in the front and back surface regions of the substrate.

8. The process of claim 7, wherein the wetted fibrous substrate is heated to a temperature greater than about 50° C. for at least about 24 hours, in order to cause phase separation to occur.

9. The process of claim 8, wherein treatment to cause phase separation includes the addition of an aqueous solution containing a salt, an acid and/or a base to the wetted fibrous substrate, prior to or after said heat treatment.

10. The process of claim 7, wherein the wetted fibrous substrate is cooled to a temperature of less than about 0° C. for at least about 24 hours, and then allowed to warm to room temperature, in order to cause phase separation to occur.

11. The process of claim 10, wherein treatment to cause phase separation includes the addition of an aqueous solution containing a salt, an acid and/or a base to the wetted fibrous substrate, prior to cooling the wetted fibrous substrate or after the cooled fibrous substrate has been warmed to room temperature.

12. The process of claim 7, further comprising forming said emulsified wetting composition by diluting a concentrated, emulsified wetting composition with an aqueous solution comprising water and a salt, an acid or a base.

13. The process of claim 7, wherein said wipe further comprises a binder formulation that is insoluble in the wetting composition and dispersible in water, said wipe being an ion-triggerable, water-dispersible wipe.

14. The process of claim 13, wherein binder formulation comprises an ion triggerable cationic polymer having the structure:

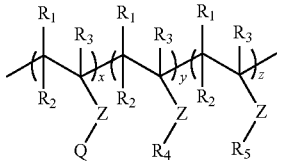

wherein: x is equal to about 1 to about 15 mole percent; y is equal to about 60 to about 99 mole percent; z is equal to 0 to about 30 mole percent; Q is selected from $C_1$ to $C_4$ alkyl ammonium, quaternary $C_1$ to $C_4$ alkyl ammonium and benzyl ammonium; Z is selected from —O—, —COO—, —OOC—, —CONH—, and —NHCO—; $R_1$, $R_2$, $R_3$ are each independently selected from hydrogen and methyl; $R_4$ is selected from methyl and ethyl; and $R_5$ is selected from hydrogen, methyl, ethyl, butyl, ethylhexyl, decyl, dodecyl, hydroxyethyl, hydroxypropyl, polyoxyethylene, and polyoxypropylene.

15. A processes for preparing a wet wipe comprising a stratified wetting composition therein, the process comprising:
forming an unstable, emulsified wetting composition by diluting a stable, concentrated, emulsified wetting composition with an aqueous solution comprising a salt, an acid or a base;
applying the unstable, emulsified wetting composition to a fibrous substrate of the wipe before phase separation within the emulsified wetting composition occurs, the fibrous substrate having a front surface region and a back surface region generally parallel thereto, and a bulk region between said front surface region and back surface region; and,
allowing phase separation of the wetting composition to occur within the wetted fibrous substrate, wherein after said phase separation, a concentration of one or more oil phase components is greater in the front and back surface regions of the substrate than a concentration of the same component, or components, in the bulk region of the substrate, and further wherein a concentration of one or more aqueous phase components is greater in the bulk region of the substrate than a concentration of the same component, or components, in the front and back surface regions of the substrate.

16. The process of claim 15, wherein said wipe further comprises a binder formulation that is insoluble in the wetting composition and dispersible in water, said wipe being an ion-triggerable, water-dispersible wipe.

17. The process of claim 16, wherein binder formulation comprises an ion triggerable cationic polymer having the structure:

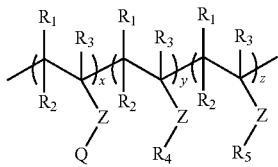

wherein: x is equal to about 1 to about 15 mole percent; y is equal to about 60 to about 99 mole percent; z is equal to 0 to about 30 mole percent; Q is selected from $C_1$ to $C_4$ alkyl ammonium, quaternary $C_1$ to $C_4$ alkyl ammonium and benzyl ammonium; Z is selected from —O—, —COO—, —OOC—, —CONH—, and —NHCO—; $R_1, R_2, R_3$ are each independently selected from hydrogen and methyl; $R_4$ is selected from methyl and ethyl; and $R_5$ is selected from hydrogen, methyl, ethyl, butyl, ethylhexyl, decyl, dodecyl, hydroxyethyl, hydroxypropyl, polyoxyethylene, and polyoxypropylene.

18. The process of claim 15, wherein the stable, concentrated, emulsified wetting composition is diluted with an aqueous solution comprising a salt, wherein the concentration of the salt in said aqueous solution is sufficient to yield a concentration of the salt in the resulting unstable wetting composition of between about 1 and about 5 weight percent, based on the total weight of the unstable wetting composition.

19. The process of claim 15, wherein the stable, concentrated, emulsified wetting composition is diluted with an aqueous solution comprising an acid, wherein the concentration of the acid in said aqueous solution is sufficient to lower the pH of the resulting unstable wetting composition to less than about 5.

20. The process of claim 15, wherein the stable, concentrated, emulsified wetting composition is diluted with an aqueous solution comprising a base, wherein the concentration of the base in said aqueous solution is sufficient to raise the pH of the resulting unstable wetting composition to greater than about 8.

* * * * *